(12) United States Patent
Lipperman et al.

(10) Patent No.: US 8,500,622 B2
(45) Date of Patent: Aug. 6, 2013

(54) VENTRICULAR FUNCTION ASSISTING DEVICE AND A METHOD AND APPARATUS FOR IMPLANTING IT

(75) Inventors: Michal Lipperman, Petach Tikva (IL); Gideon Meyer-Brodnitz, Haifa (IL); Lior Rosen, Tel-Aviv (IL); Remo Eyal Almog, Tel-Aviv (IL); Amit Tubishevitz, Tel-Aviv (IL)

(73) Assignee: Corassist Cardiovascular Ltd., Herzliya Pituach (IL)

( * ) Notice: Subject to any disclaimer, the term of this patent is extended or adjusted under 35 U.S.C. 154(b) by 0 days.

(21) Appl. No.: 12/998,429

(22) PCT Filed: Oct. 20, 2009

(86) PCT No.: PCT/IL2009/000988
§ 371 (c)(1), (2), (4) Date: Jun. 27, 2011

(87) PCT Pub. No.: WO2010/046895
PCT Pub. Date: Apr. 29, 2010

(65) Prior Publication Data
US 2011/0257461 A1      Oct. 20, 2011

Related U.S. Application Data

(60) Provisional application No. 61/106,621, filed on Oct. 20, 2008.

(51) Int. Cl.
*A61N 1/362* (2006.01)

(52) U.S. Cl.
USPC .............................................. 600/16

(58) Field of Classification Search
USPC ..................................... 600/16–18
See application file for complete search history.

(56) References Cited

U.S. PATENT DOCUMENTS

| | | |
|---|---|---|
| 2005/0113810 A1 | 5/2005 | Houser et al. |
| 2006/0025800 A1 | 2/2006 | Suresh |
| 2008/0086164 A1 | 4/2008 | Rowe |

OTHER PUBLICATIONS

International Search Report for PCT/IL2009/000988, mailed Feb. 3, 2010.
Written Opinion of the International Searching Authority for PCT/IL2009/000988, mailed Feb. 3, 2010.

*Primary Examiner* — Brian T Gedeon
(74) *Attorney, Agent, or Firm* — Nixon & Vanderhye PC

(57) ABSTRACT

The present invention provides a ventricular function assisting device configured to be implanted in a heart ventricle designed in a form of flower-like configuration comprising two or more petals attached at a base section, said petals comprise elastic elements and/or portions capable of being elastically bent in radial directions and optionally also in sideway and/or longitudinal directions, which allow changing the state of the device between: i) a folded conformation, in which its petals are radially pressed inwardly towards each other to assume a reduced diameter of its flower-like configuration; and ii) a deployed conformation, in which the petals are opened in a radial outward direction as the device is discharged from the delivery tube or sheath into a heart ventricle and implanted thereinside in a preloaded state.

21 Claims, 28 Drawing Sheets

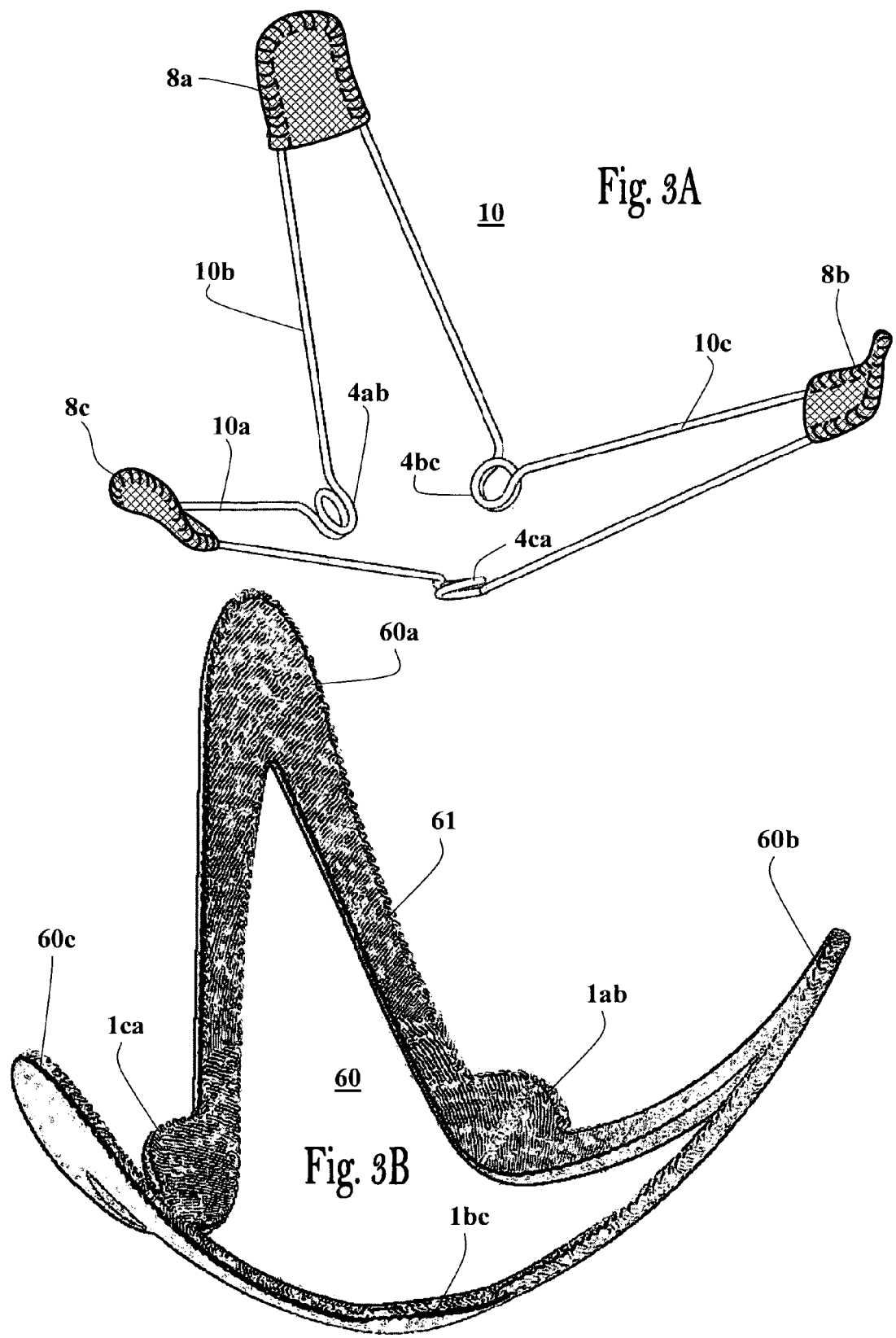

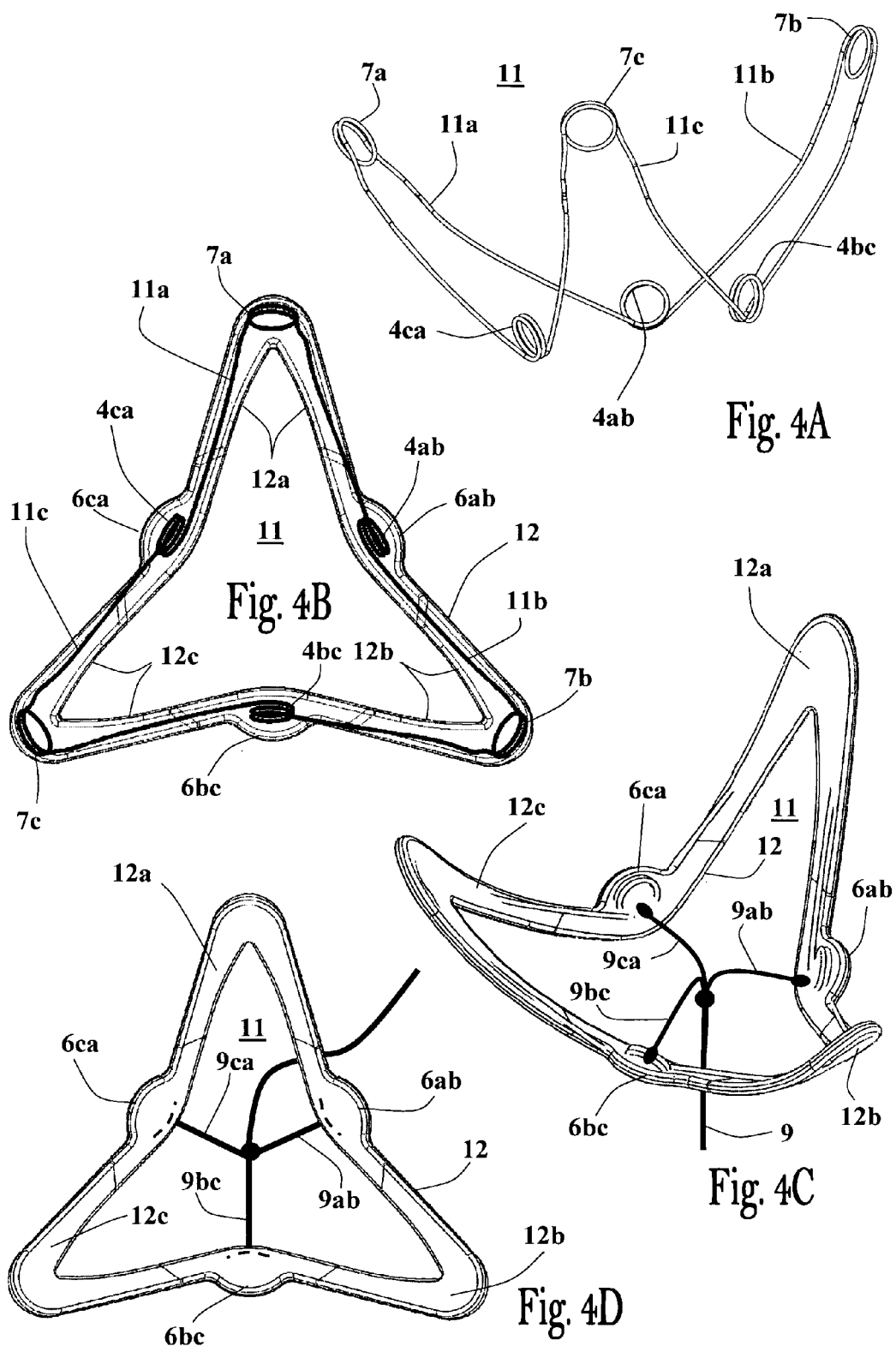

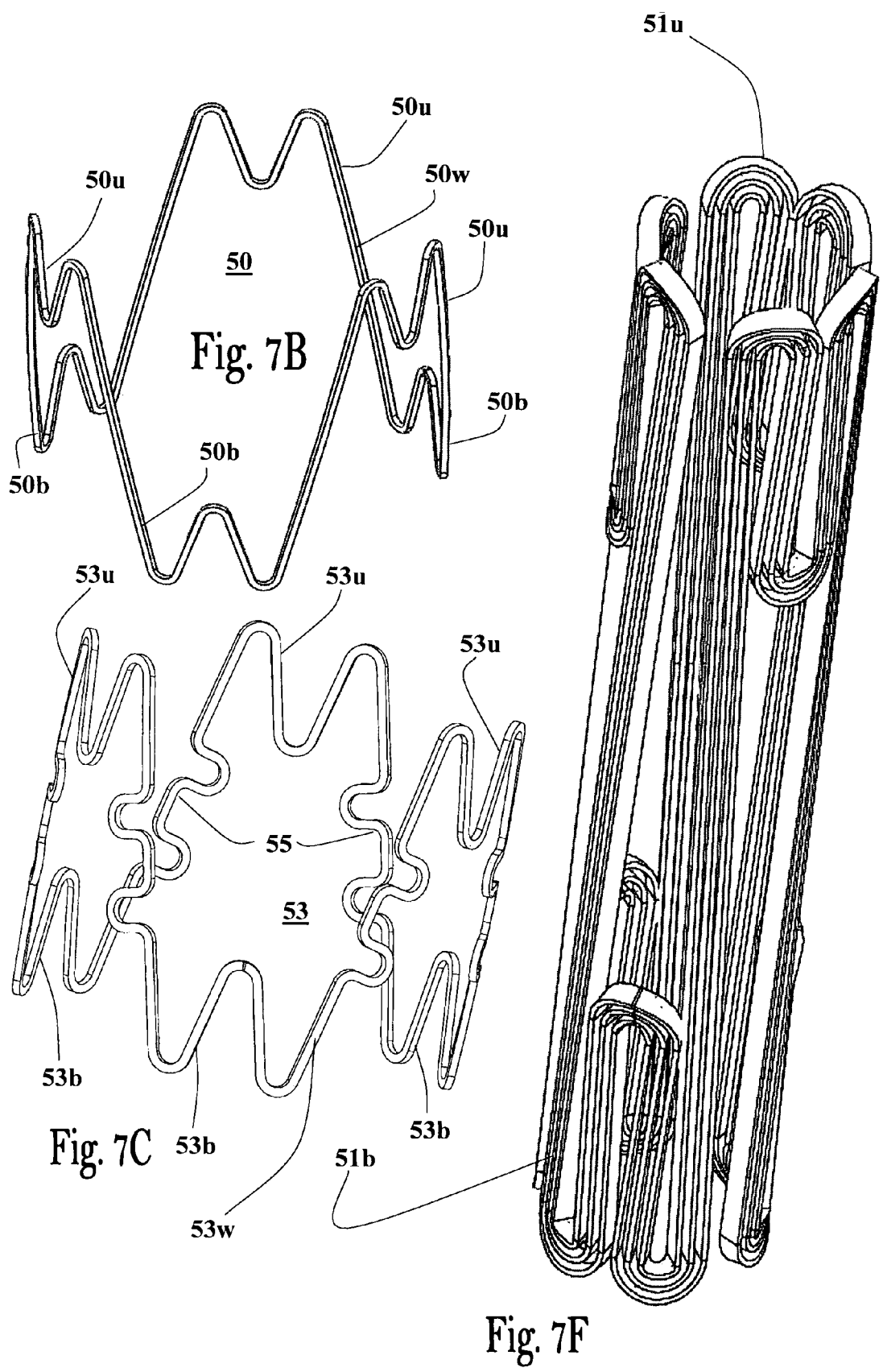

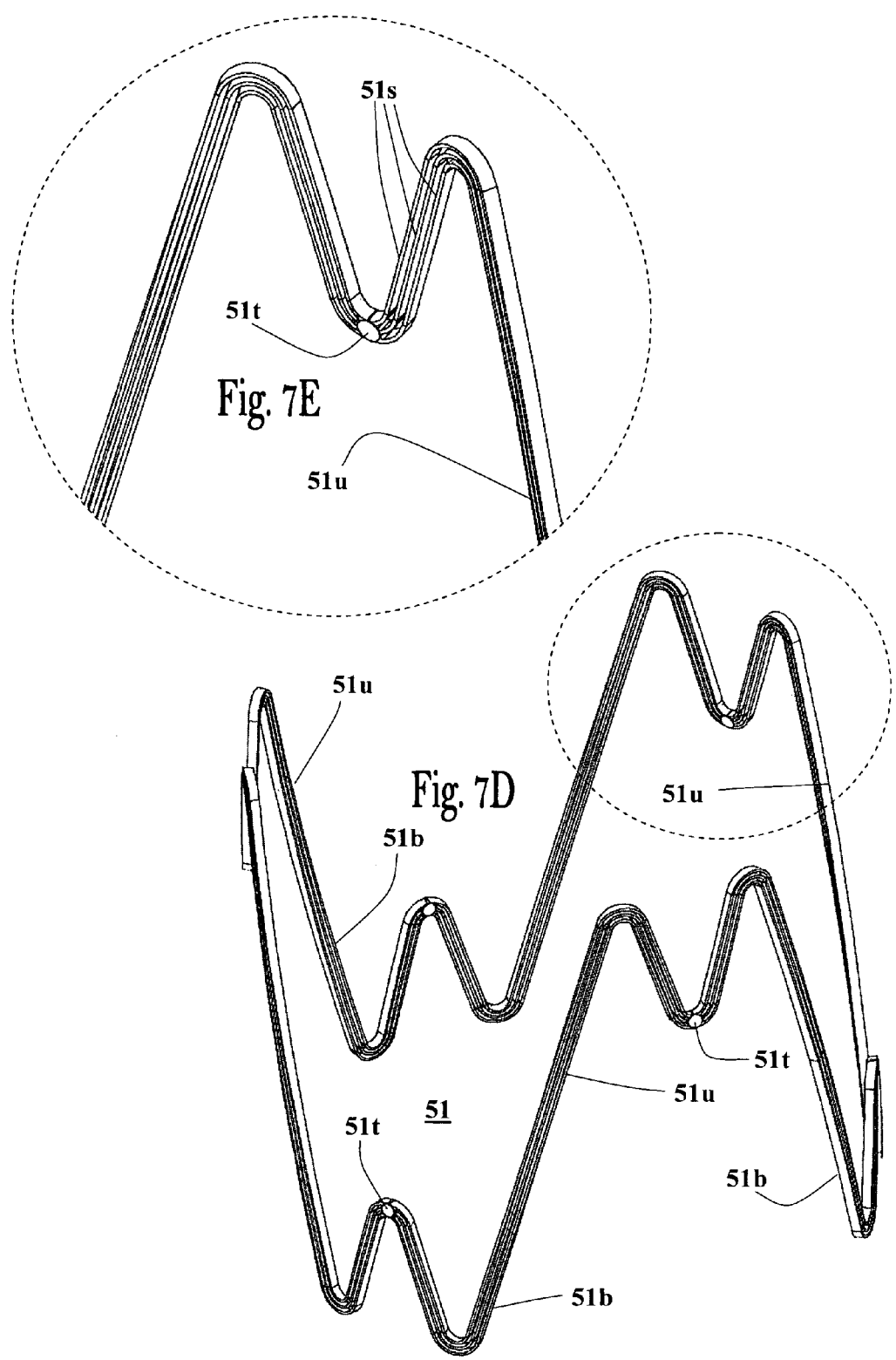

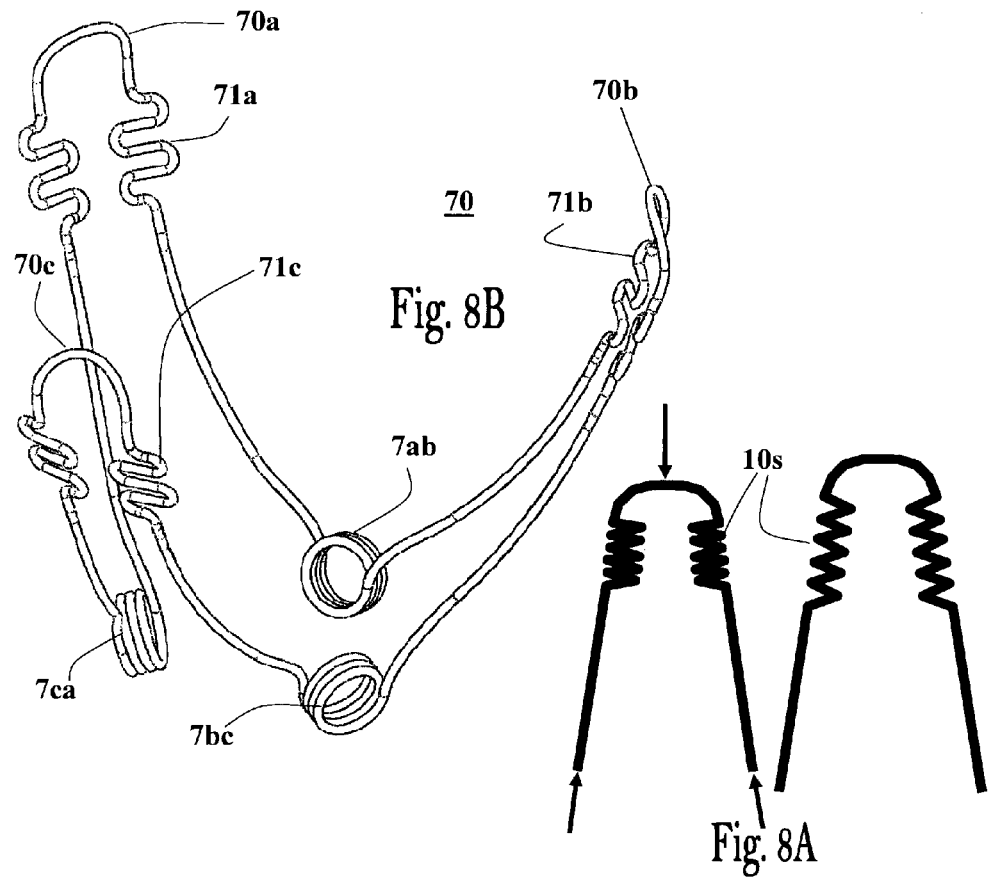
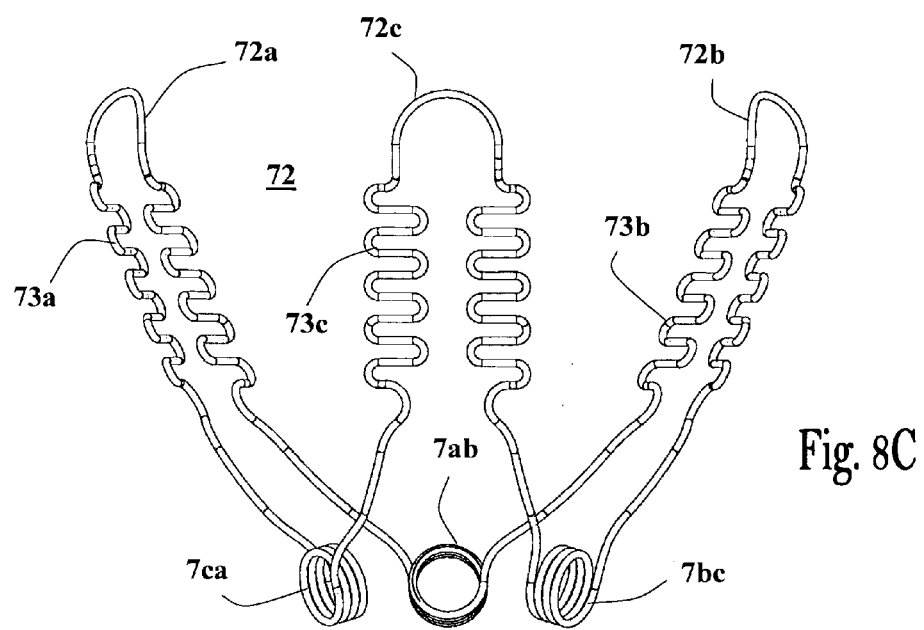

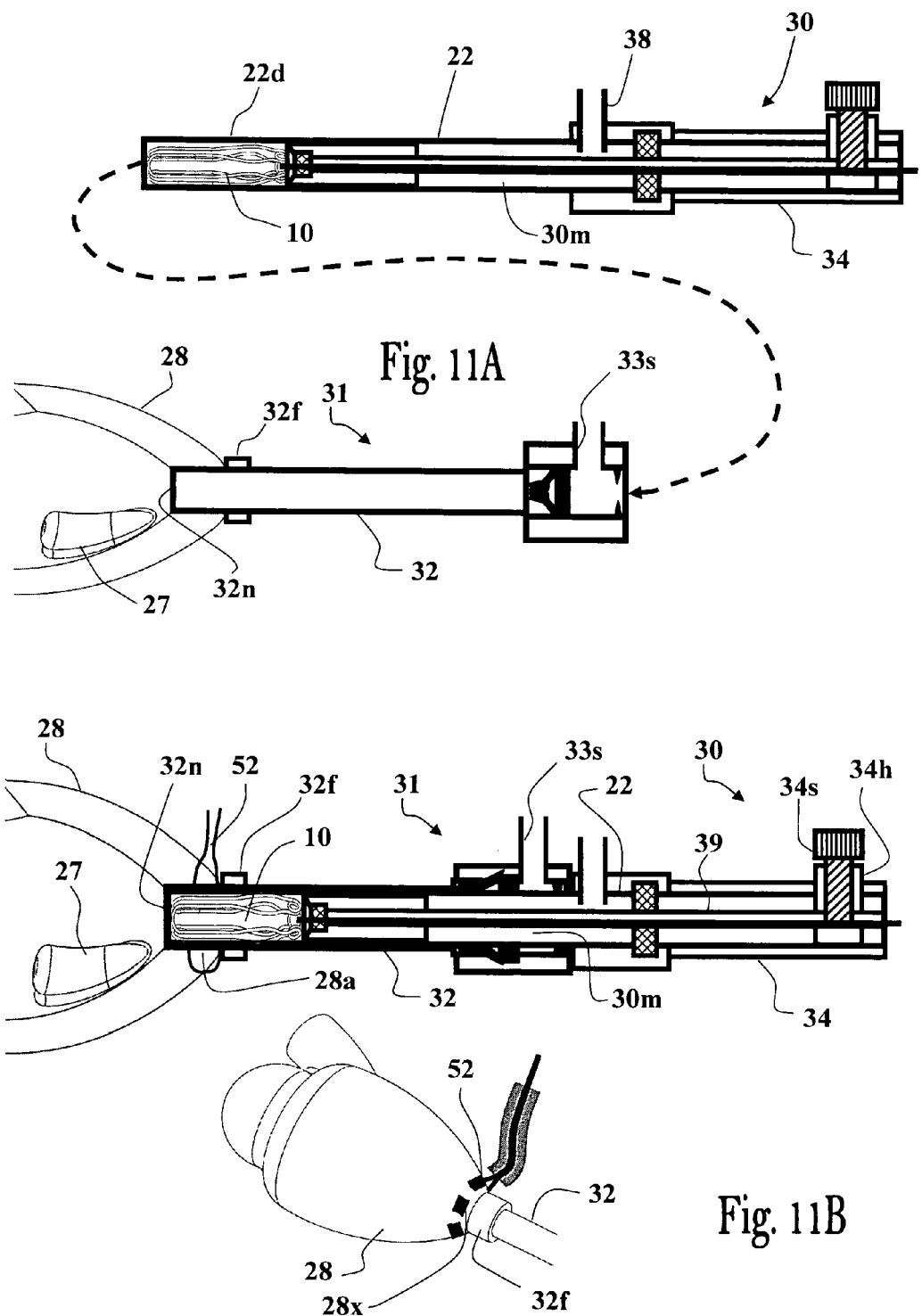

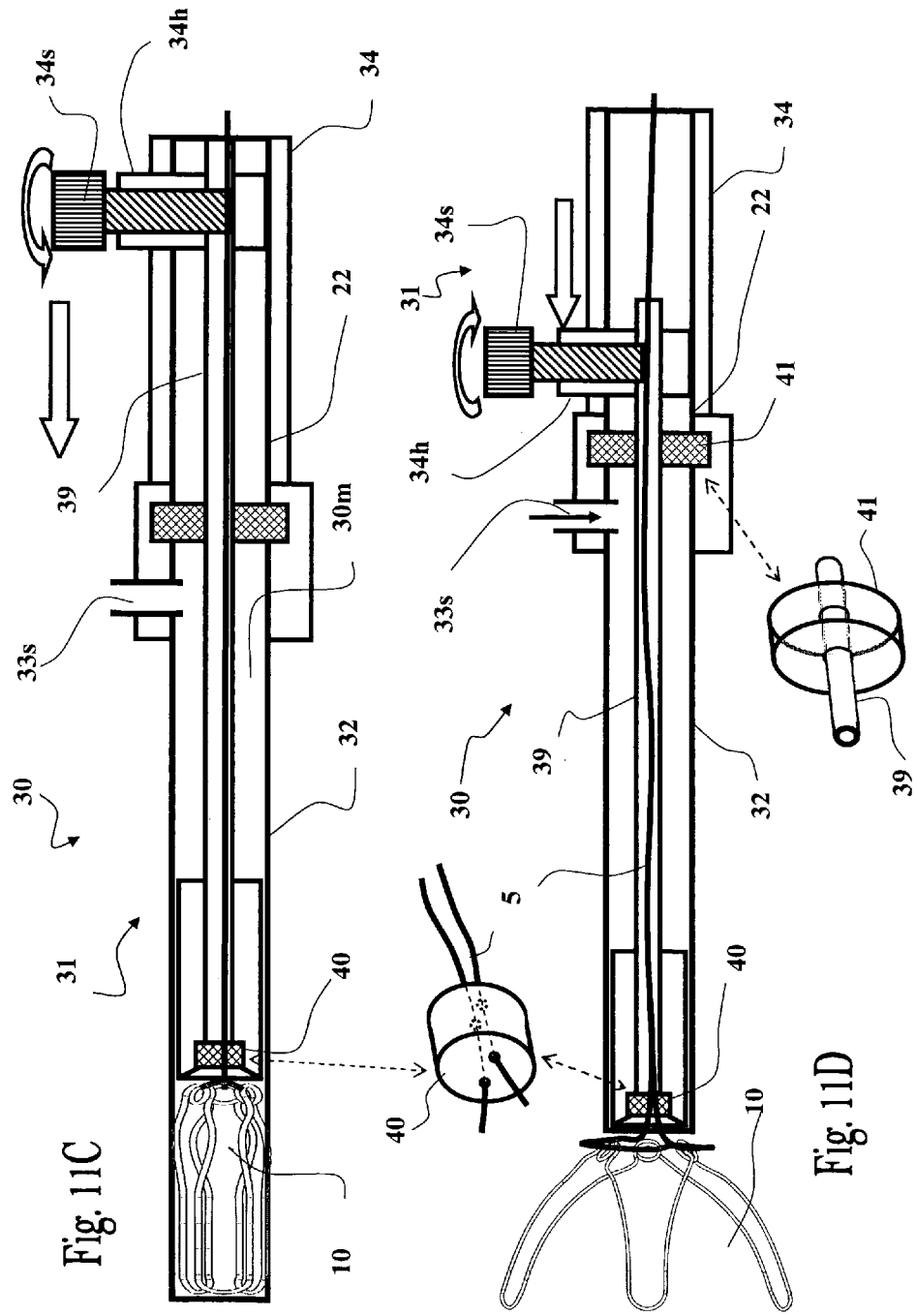

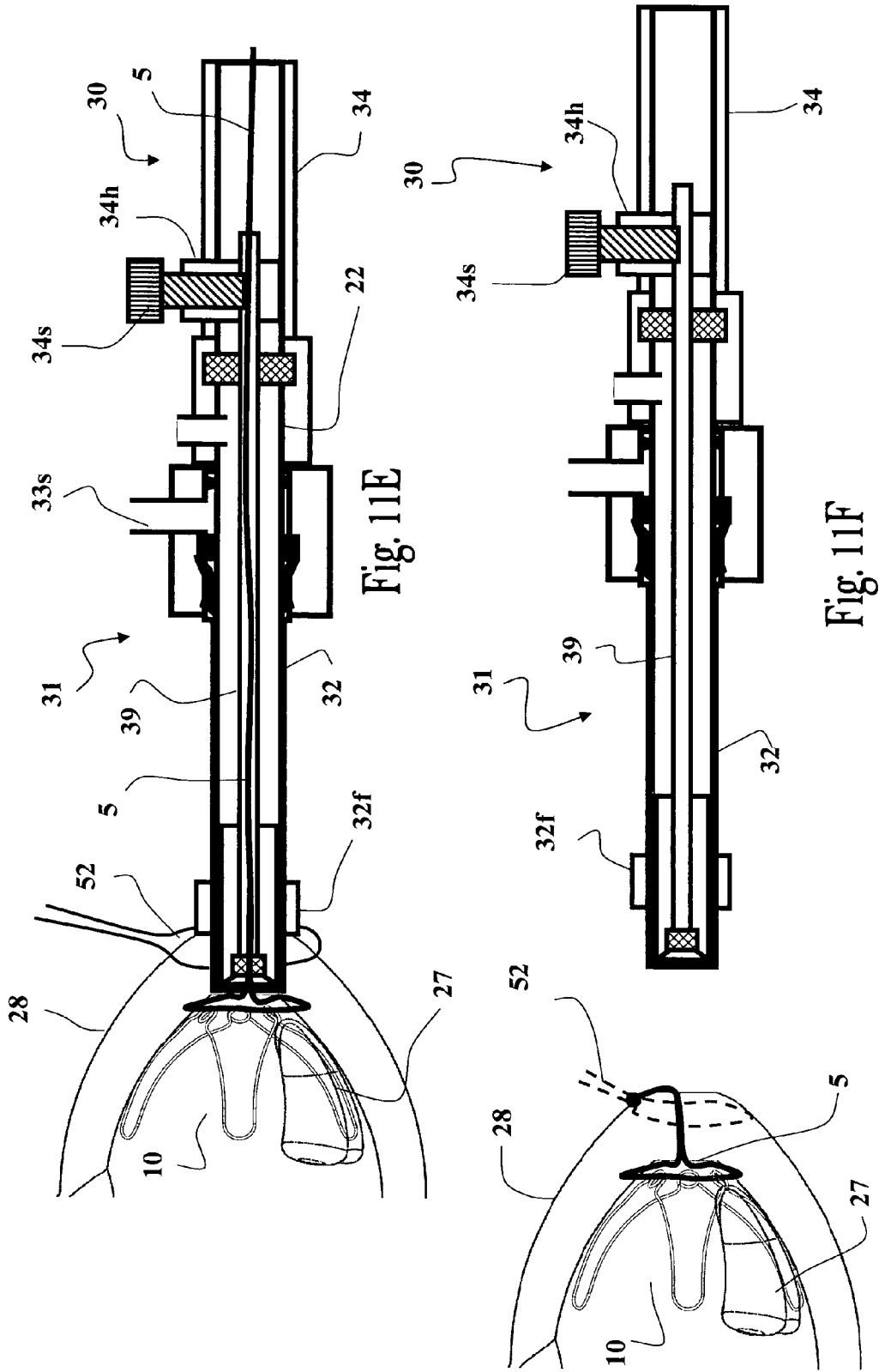

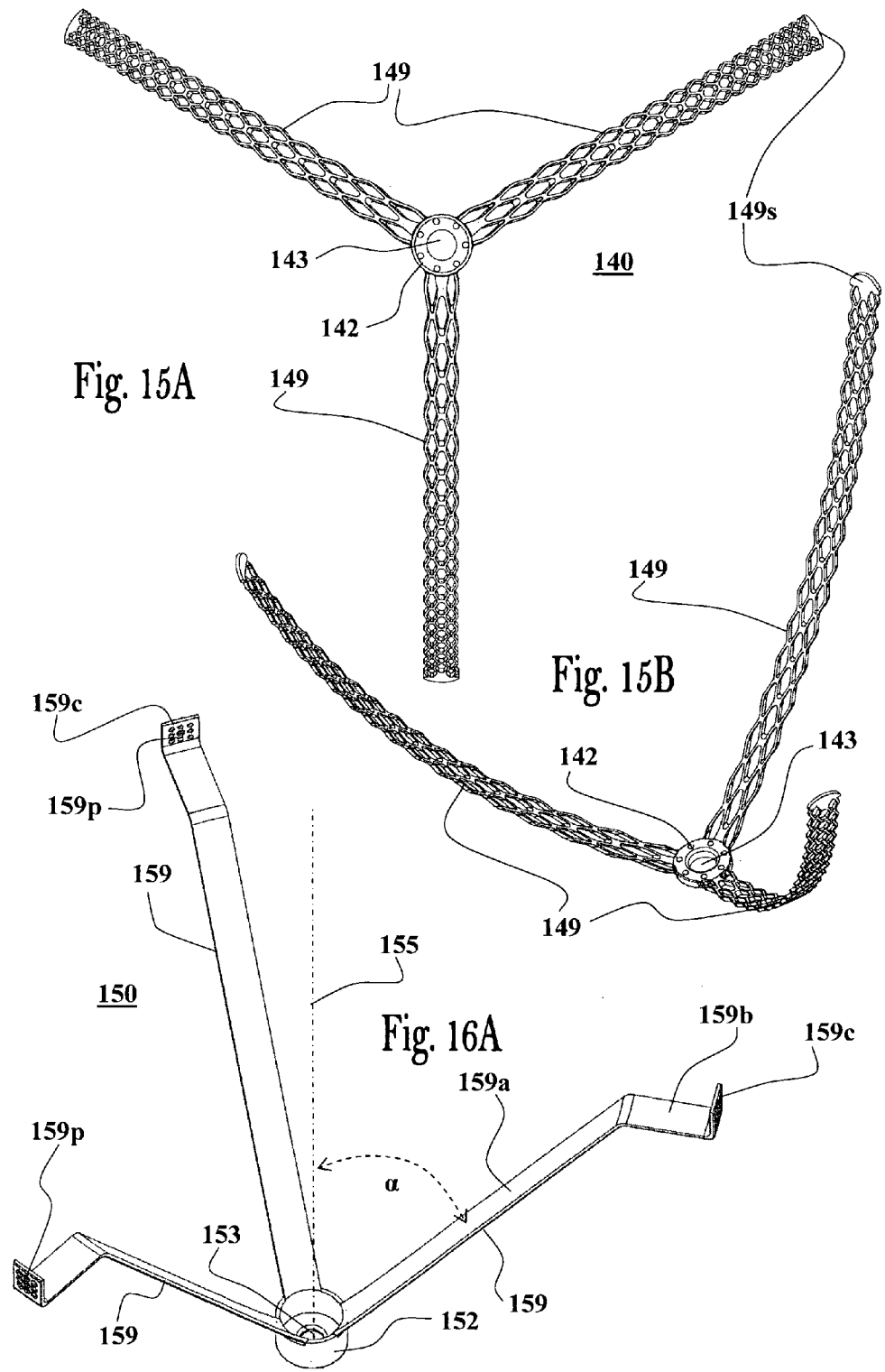

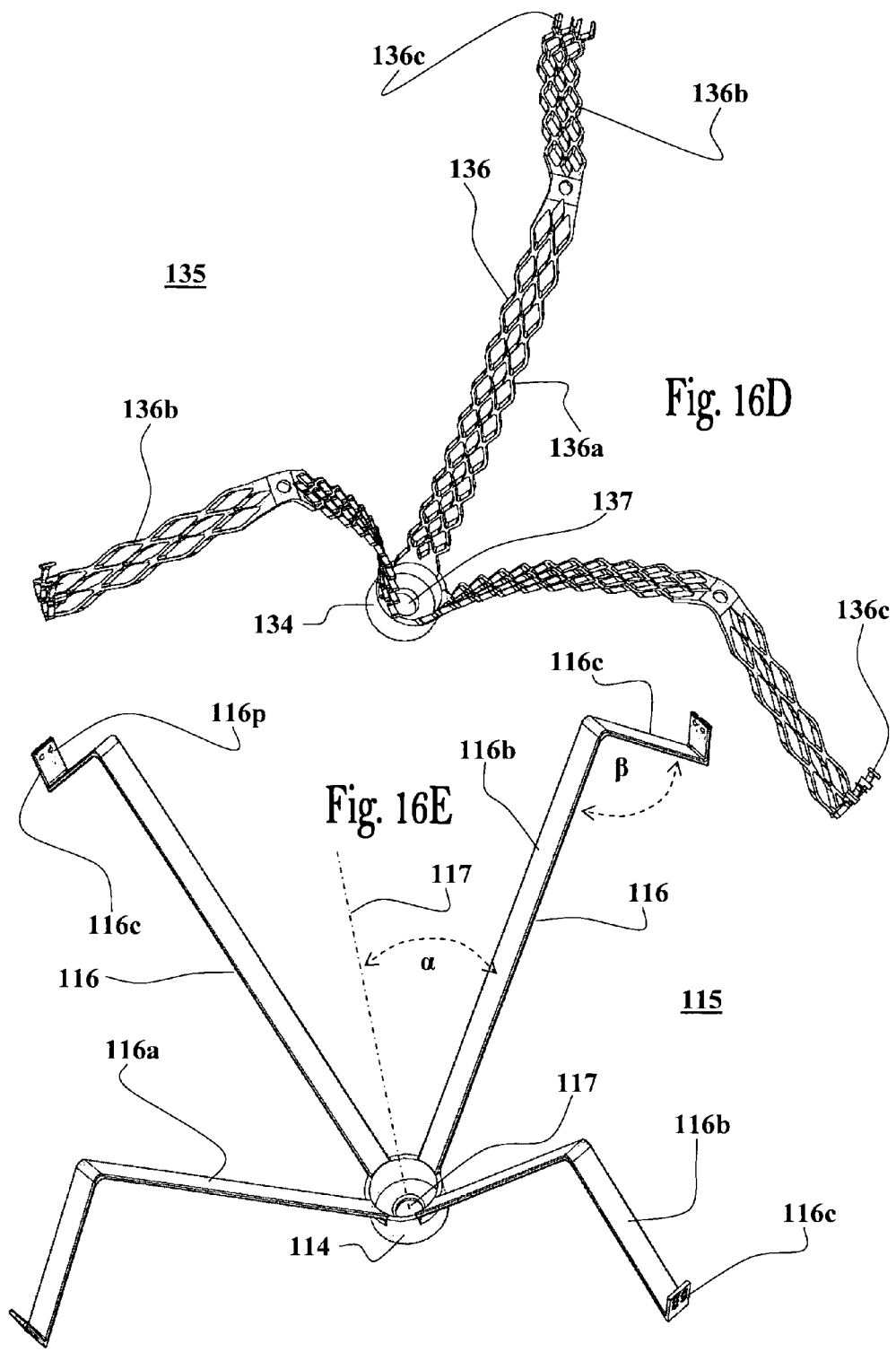

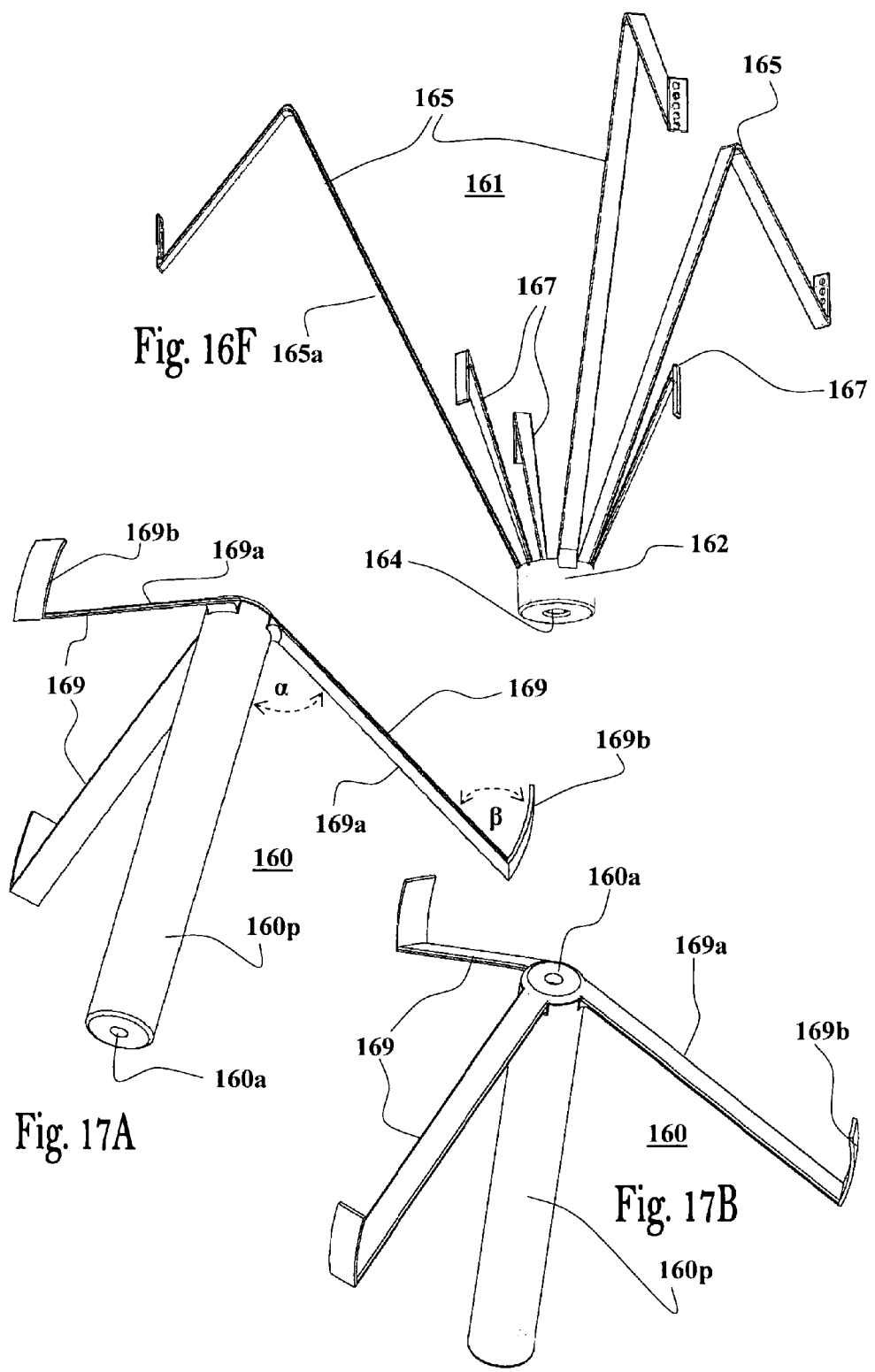

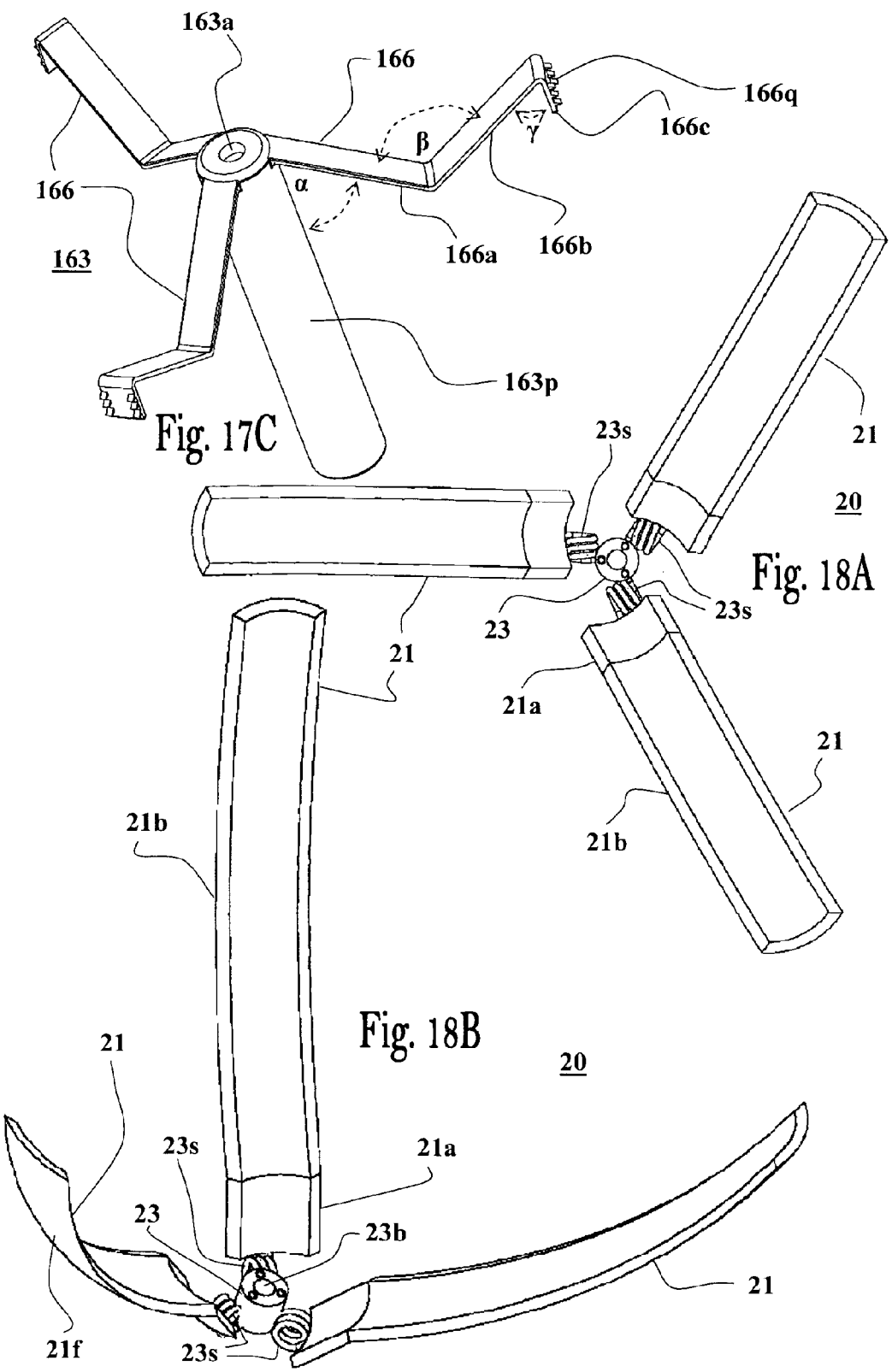

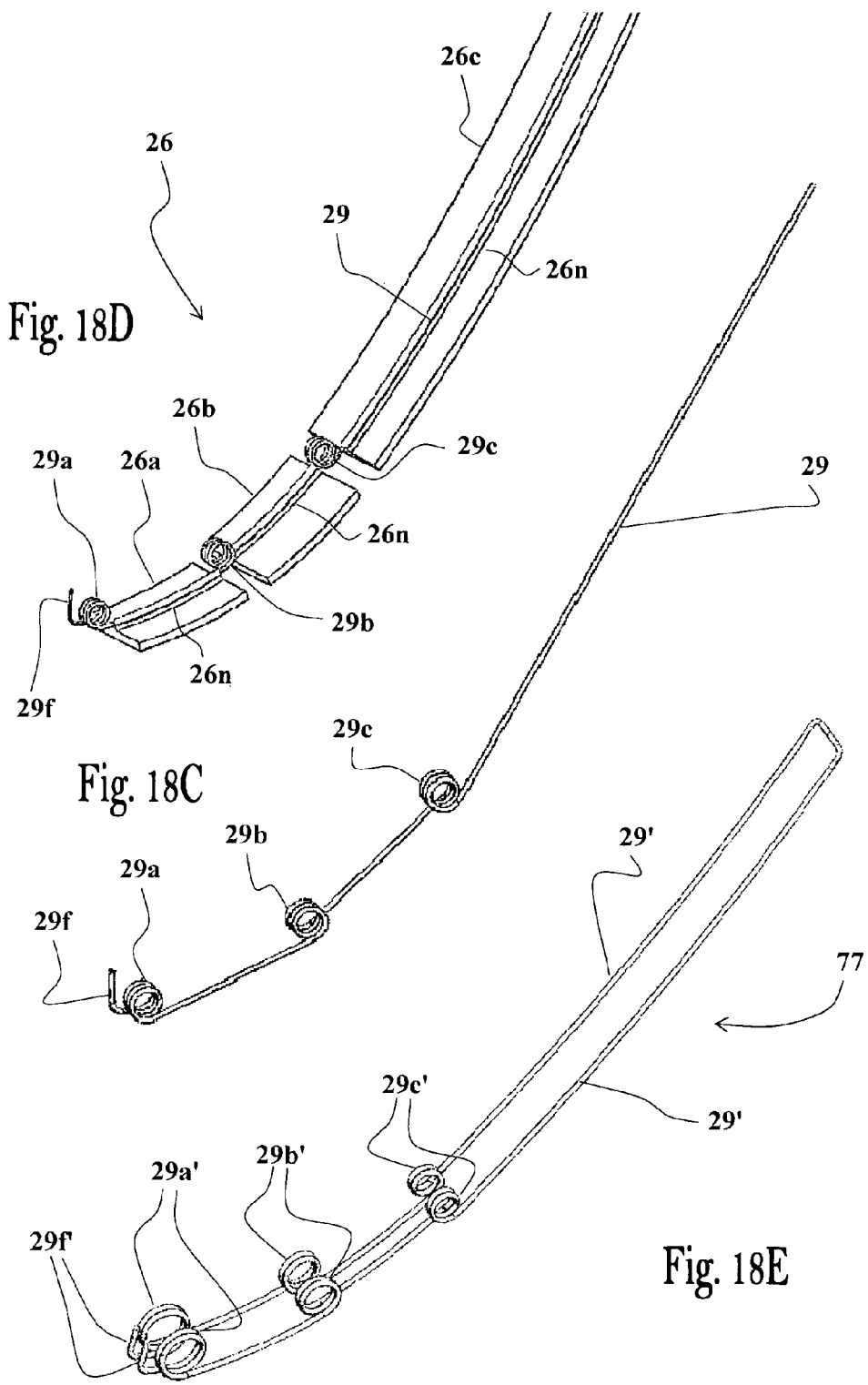

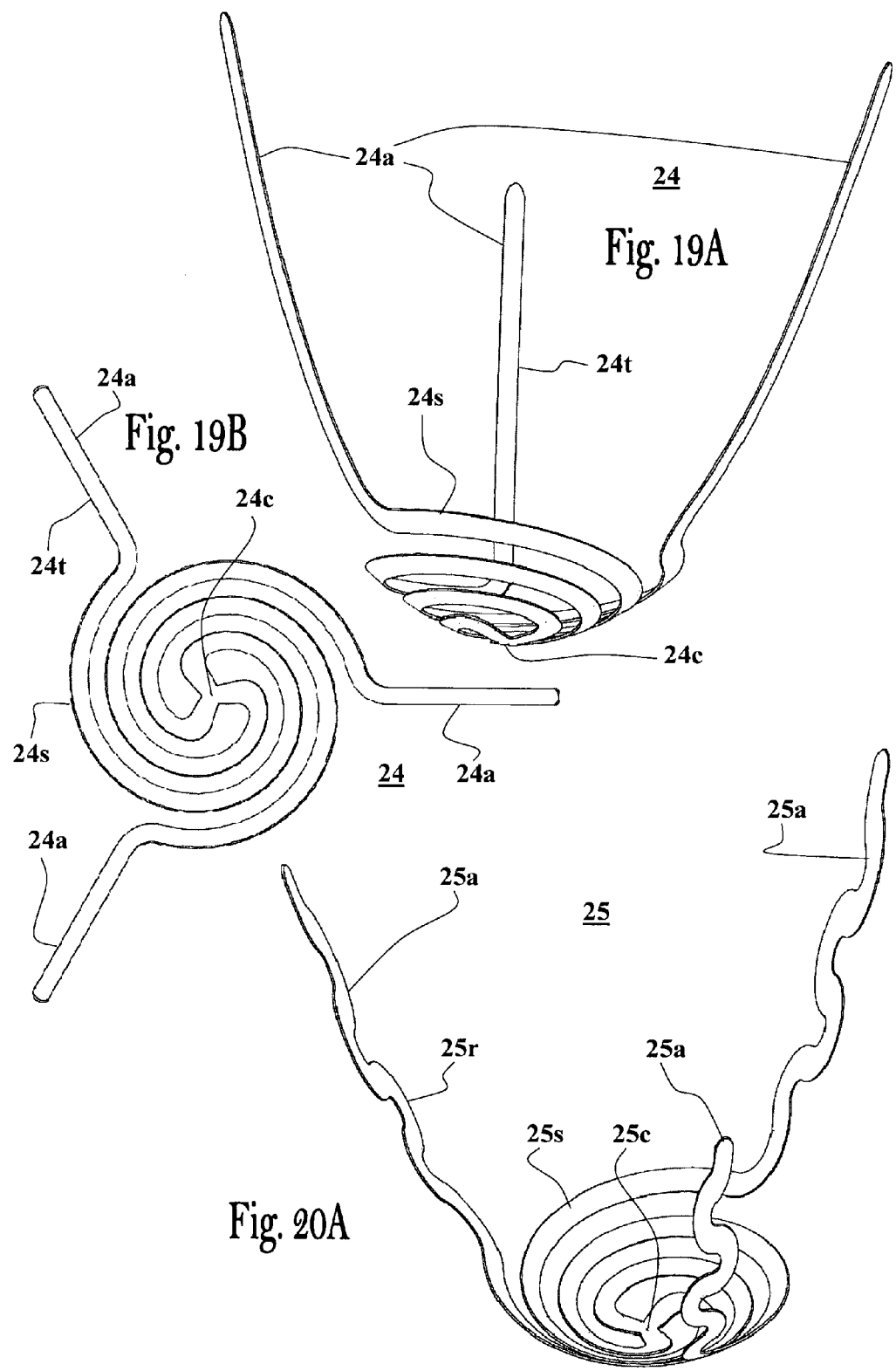

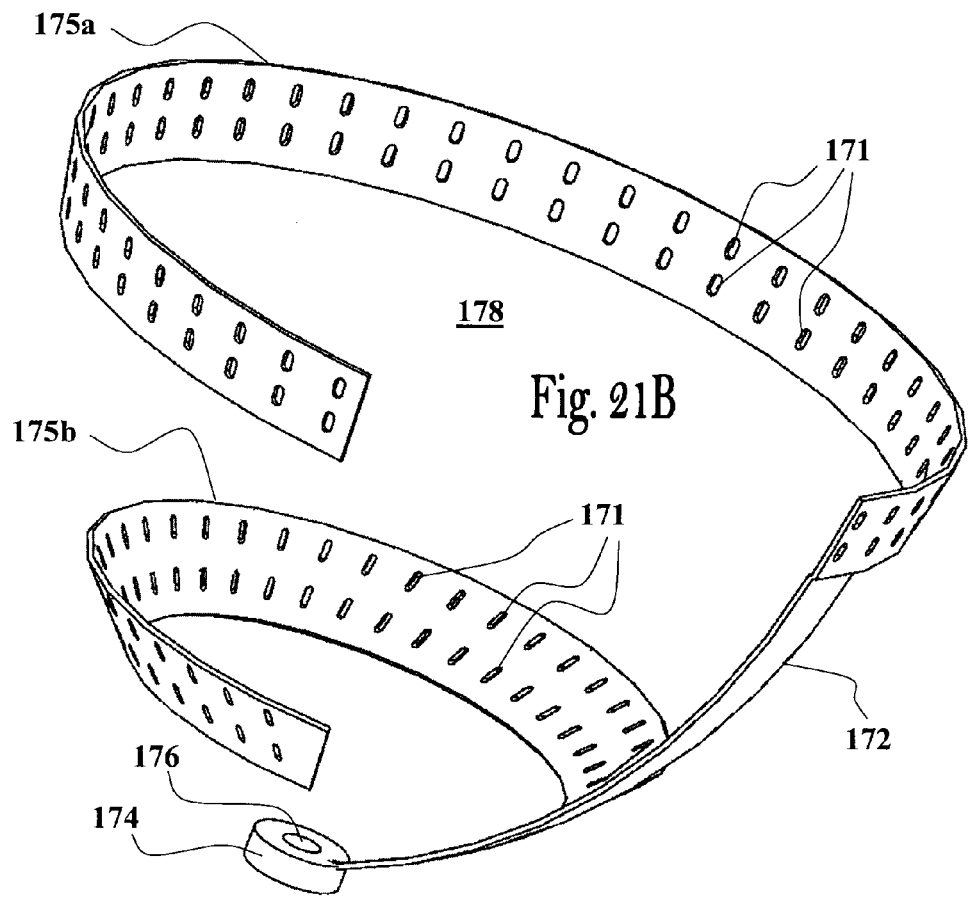
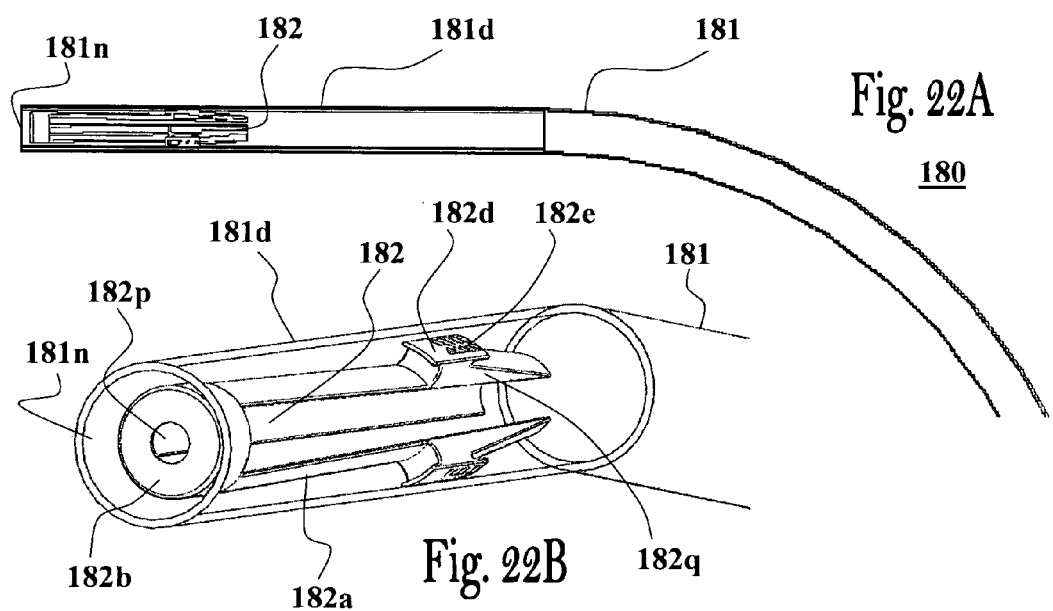

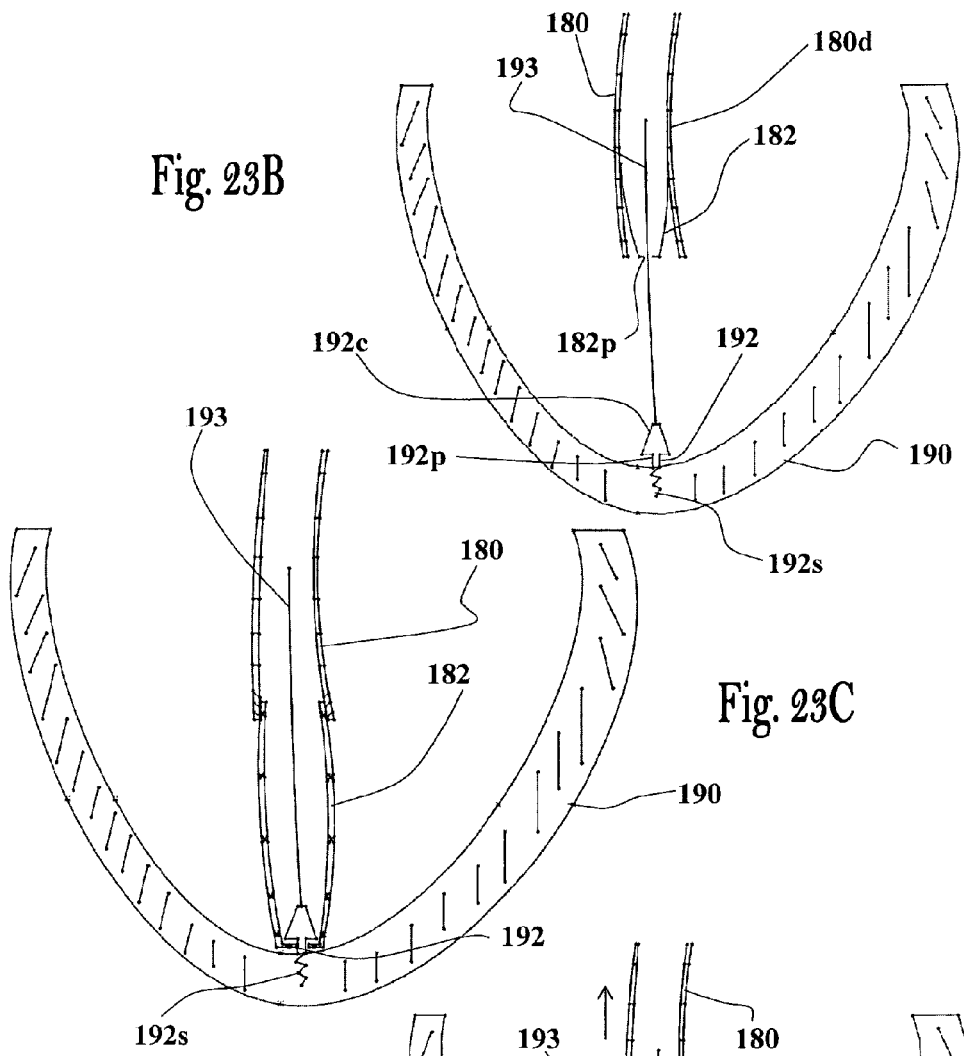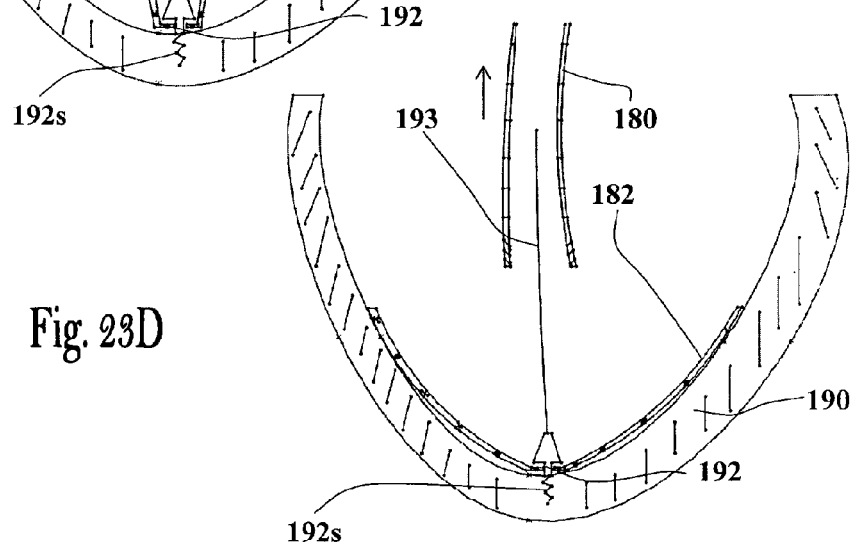

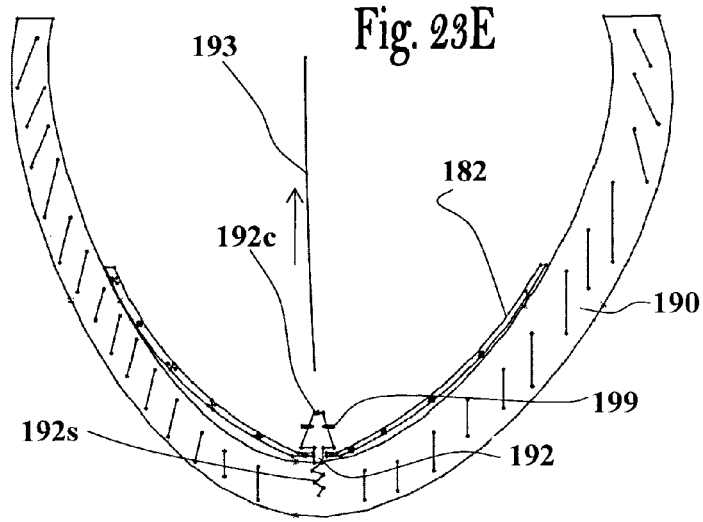
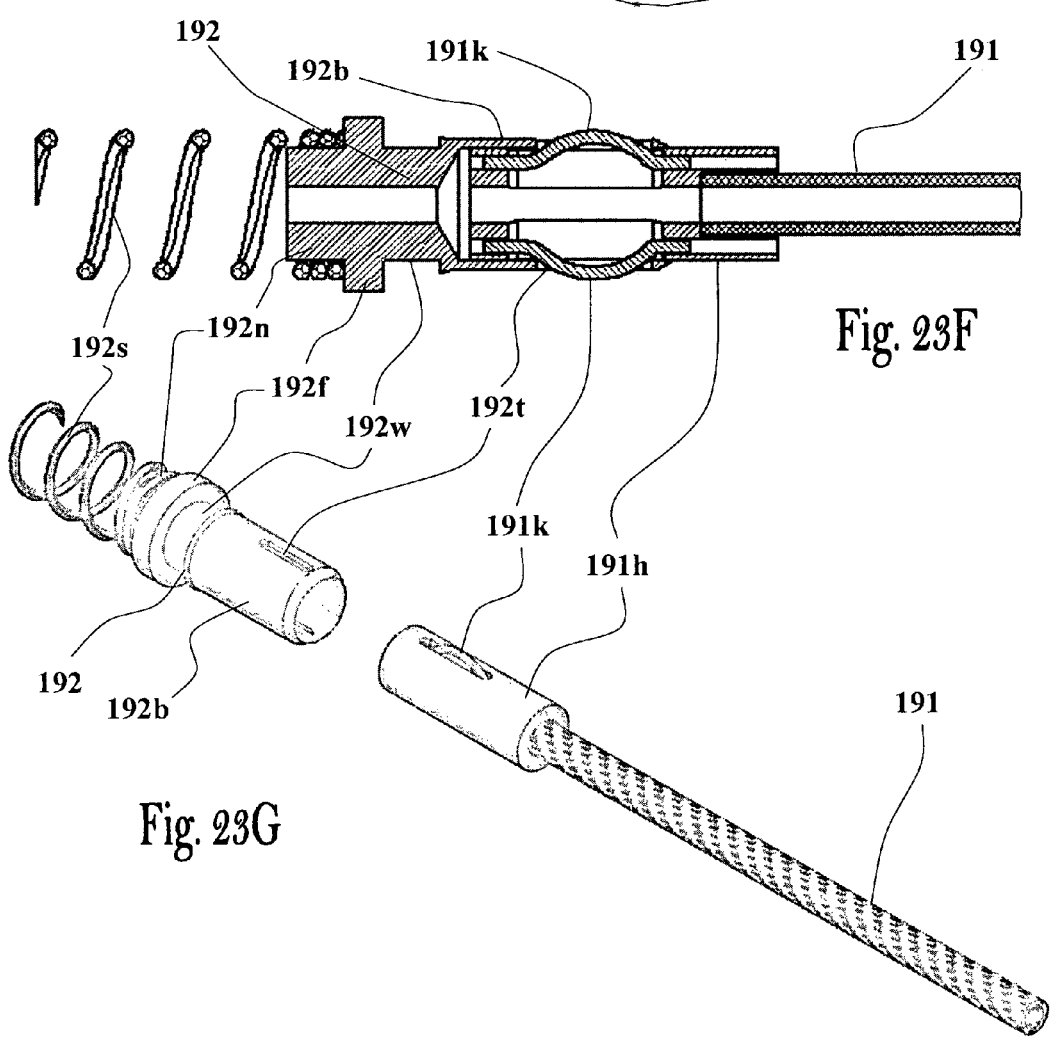

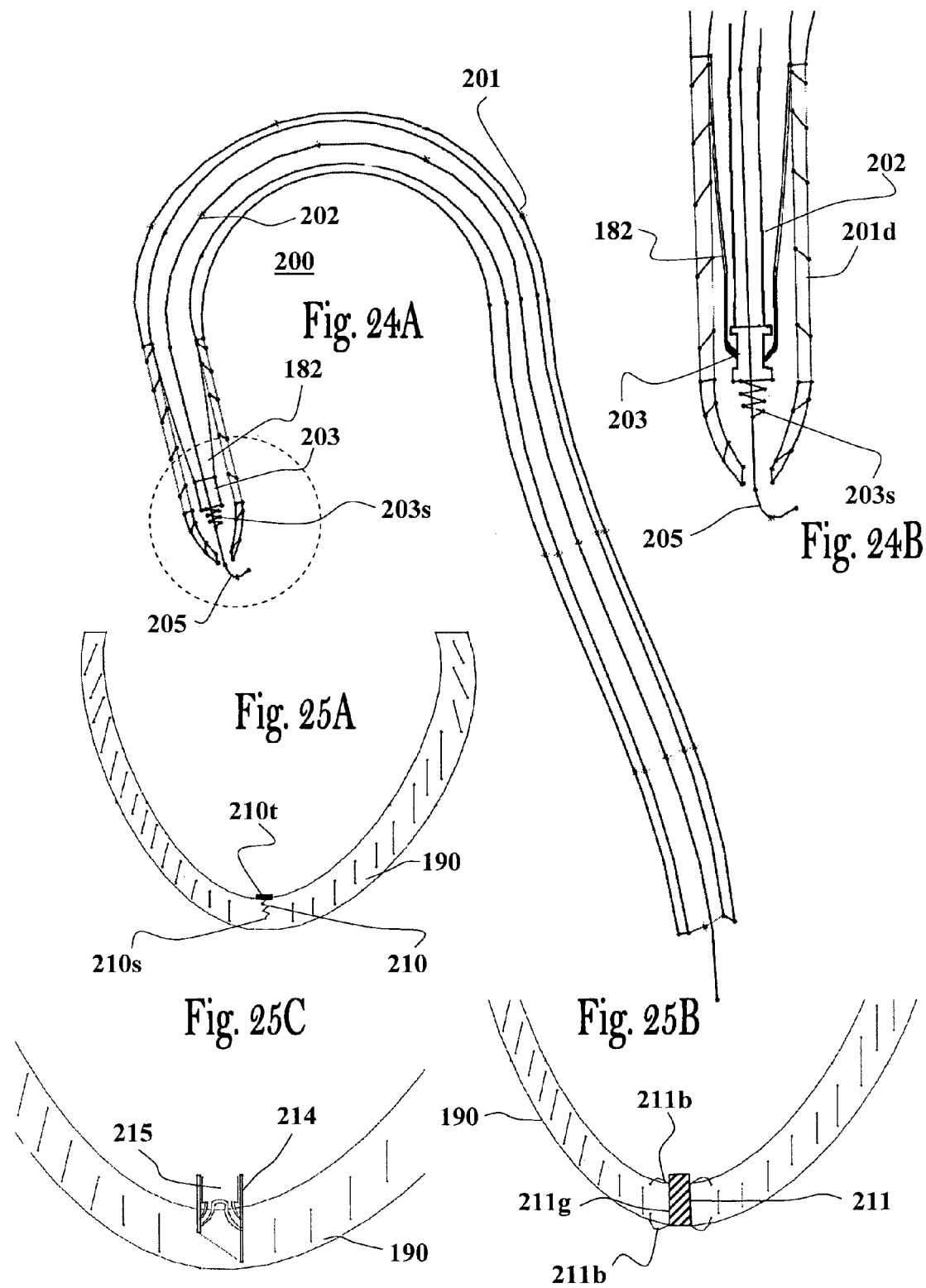

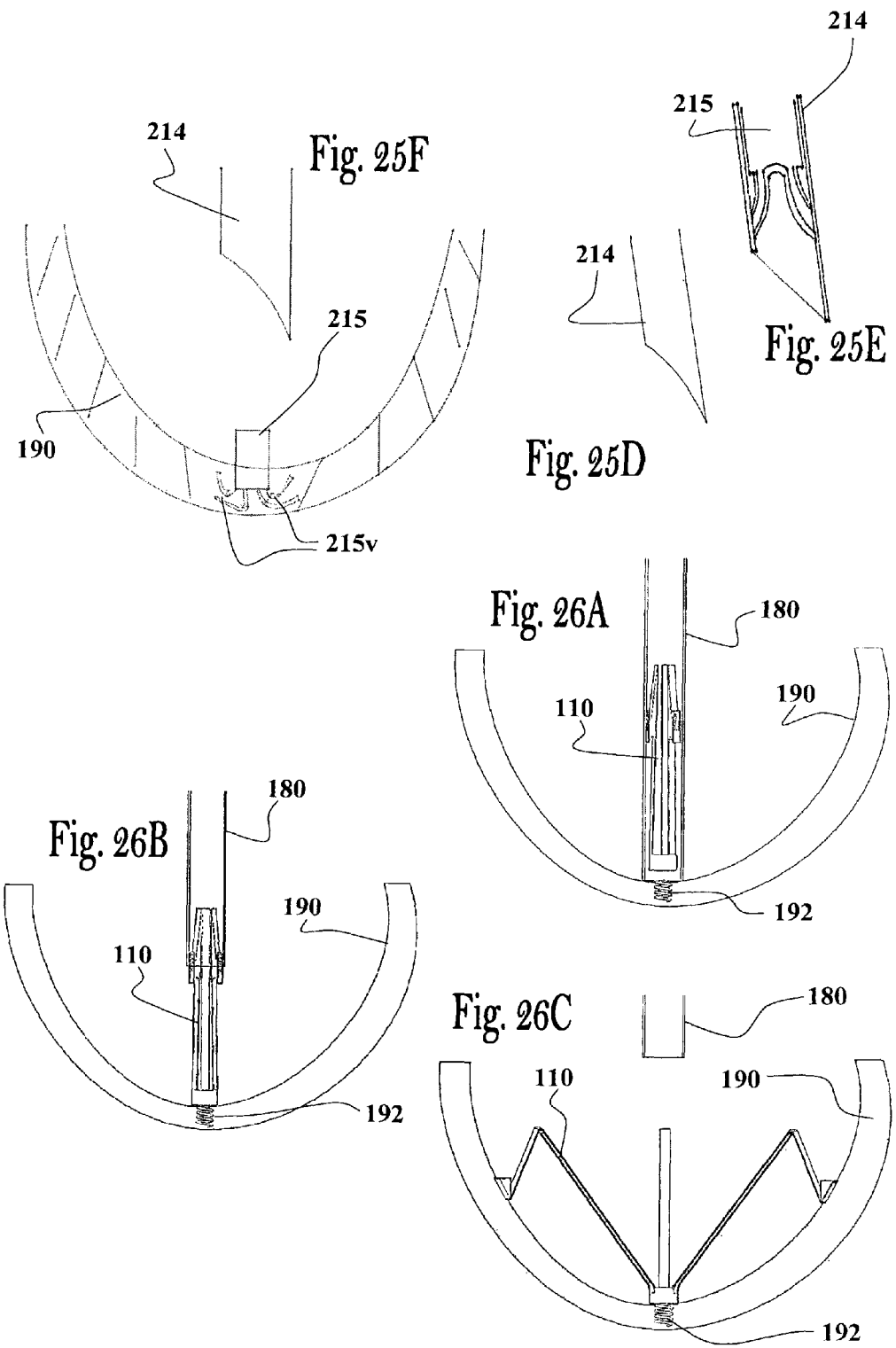

VENTRICULAR FUNCTION ASSISTING DEVICE AND A METHOD AND APPARATUS FOR IMPLANTING IT

This application is the U.S. national phase of International Application No. PCT/IL2009/000988, filed 20 Oct. 2009, which designated the U.S. and claims the benefit of U.S. Provisional No. 61/106,621, filed 20 Oct. 2008, the entire contents of each of which are hereby incorporated by reference.

FIELD OF THE INVENTION

The present invention generally relates to a method and device for assisting a malfunctioning heart. More particularly, the invention relates to a device for improving the heart's left ventricular function, and to a method and apparatus for implanting said device in a treated heart.

BACKGROUND OF THE INVENTION

Diastolic heart failure (DHF), a subset of congestive heart failure (CHF), is a clinical syndrome resulting from any structural or functional cardiac disorder that impairs the ability of the ventricle relax properly and fill with blood. The hospitalization rate of the patients suffering from DHF diastolic heart failure is similar to the hospitalization rate of patients suffering from systolic heart failure (SHF—a condition in which the heart is not contracting efficiently).

Primary diastolic dysfunction is typically observed in patients with hypertension and hypertrophic or restrictive cardiomyopathy, but can also occur in a variety of other clinical disorders and has a particularly high prevalence in the elderly population. Aging is associated with 'physiologic' diastolic dysfunction due to the increase in left ventricle muscle mass and/or changes in passive elastic properties of the myocardium, hence, the concern of an increase in the incidence of diastolic dysfunction as the aging of the western world population progresses.

To one of ordinary skill in the art, there is thus a need for, and it would be highly advantageous to have a method and device for improving heart ventricular function. Moreover, there is a need for such a method and device which is biocompatible and is specially configured for compact and long-term reliable use in humans.

Various in-vivo methods and devices for improving diastolic function of the heart are described in international patent applications Nos. PCT/IL02/00547 (WO 03/007778), PCT/IL05/01014 (WO 06/03310), PCT/IL04/00986 (WO 05/041745), PCT/IL04/00072 (WO 04/066805), PCT/IL2007/001180 (WO 08/038276) of the same assignee hereof, the descriptions of which are incorporated herein by reference. The aforementioned international patent applications describe elastic means used for improving diastolic function of the left ventricle of the heart by pushing and/or pulling, an inner and/or outer wall region respectively of the ventricle during the cardiac cycle while minimally disturbing the heart function. The operation of the devices described in these publications is based on storing energy from the myocardium during the systole and releasing it during diastole, thereby making it available to augment diastolic performance.

The present invention provides a device and a method for implanting it inside the left ventricle cavity, for assisting left ventricular function of the heart, which may be used independently, or in combination with imaging modalities such as Echocardiography and/or X-Ray Fluoroscopy.

It is therefore an object of the present invention to provide a method and device for augmenting diastolic performance in diastolic heart failure (DHF) patients.

It is another object of the present invention to provide a method and apparatus for implanting the ventricular function assisting device of the invention.

It is a further object of the present invention to provide minimally invasive methods for implanting the ventricular function assisting device of the invention through trans apical approach or through catheterization.

It is yet another object of the present invention to provide an imaging method and technique for guiding the implantation of the ventricular function assisting device of the invention in the left ventricle based on the inner morphology of the ventricle.

Other objects and advantages of the invention will become apparent as the description proceeds.

BRIEF DESCRIPTION OF THE DRAWINGS

The present invention is illustrated by way of example in the accompanying drawings, in which similar references consistently indicate similar elements and in which:

FIGS. 1A and 1B show an embodiment of a ventricular function assisting device of the invention comprising three-arms, wherein FIG. 1A shows a perspective view of the device with base point loops in an opened (free) state and FIG. 1B shows a perspective view of such device in a folded state;

FIGS. 3A and 3B show perspective views of a three-arms ventricular function assisting device of the invention, wherein the device in FIG. 3A comprises a biocompatible fabric material attached over the top end section of the arms of the device and in FIG. 3B the entire device is covered with such biocompatible fabric.

FIGS. 4A to 4D show another preferred embodiment of a three-arms ventricular function assisting device of the invention having base and vertex torsion loops, wherein FIG. 4A is a perspective view of the device, FIG. 4B is a top transparent view of the device encased inside a padding cover, FIG. 4C shows a perspective view of the device encased in the padding cover having fixation suture strings attached to the base torsion loops through the padding cover, and FIG. 4D shows a top view of the device having fixation suture strings attached to the padding cover near the base torsion loops;

FIGS. 5A to 5D show various possibilities for configuring the ventricular function assisting device of the invention, wherein FIG. 5A shows side and perspective views of a four-arms configuration in which the arms are curved outwardly, FIG. 5B shows side and perspective views of a four-arms configuration in which the arms are curved inwardly, FIG. 5C shows side and perspective views of a four-arms configuration having straightened arms, and FIG. 5D shows side and perspective views of a three-arms configuration having slanted arms;

FIGS. 6A to 6C show various configurations for the base and/or vertex (upper) points of the arms of the ventricular function assisting device of the invention, wherein FIG. 6A shows a "V"-like shape base point configuration made without loops, FIG. 6B shows a "V"-like shape base point configuration comprising one or more torsion loops (multi-turn loops), and FIG. 6C shows a base point configuration comprising a single crossed loop (single loop);

FIGS. 7A to 7F show a configuration of a ventricular function assisting device of the invention that may be produced by laser cut, wherein FIGS. 7A and 7B respectively show side and perspective views of a ventricular function assisting device of the invention which may be cut from a tube wherein the cuts are having a rectangular cross section, FIG. 7C shows a perspective view of a configuration having "Ω"-like shaped torsion sections in its arms, FIG. 7D shows a cut pattern in a opened deployed state wherein the arms of the device are formed by a laser cut forming a multi layered strip, FIG. 7E shows a close-up of a vertex of an arm in such multi layered strip configuration, and FIG. 7F shows the multi layered strip device in a folded conformation;

FIG. 8A to 8E show implementations of the arms of the ventricular function assisting device of the invention with elastic elements, wherein FIG. 8A schematically illustrates an embodiment of the arms of the device by means of a wire having corrugated sections forming spring like structures, FIGS. 8B and 8C show a perspective view of three-arms embodiments of the device of the invention having base torsion loops and corrugated sections forming spring structures in the arms of the device, FIG. 8D is a perspective view of a three-arms embodiment having corrugated sections forming spring structures in the arms and base sections of the device, and FIG. 8E schematically illustrates an embodiment of the arms of the device comprising pistons.

FIGS. 9A and 9B demonstrate a preferred method for establishing a direct channel to the left ventricle trough a trans apical approach, by means of a trans apical sheath (tube), and a dilator, wherein FIG. 9A shows general structures of a trans-apical sheath and dilator which may be used in approaching the heart, and FIG. 9B shows the trans-apical sheath and dilator when the channel is established;

FIGS. 11A to 11F demonstrate a procedure for introducing a ventricular function assisting device of the invention by means of the delivery tool and trans apical sheath used in the trans apical approach into the left ventricle, wherein FIG. 11A illustrates insertion of the delivery tool with the ventricular function assisting device into the trans apical sheath, FIG. 11B shows a portion of the trans apical sheath introduced into the left ventricle with the delivery tool and the ventricular function assisting device inside its delivery tube in a folded state before released into the left ventricle, FIG. 11C shows the delivery tool and the ventricular function assisting device contained thereinside in a folded state and the mechanism of releasing the device from the delivery tool, FIGS. 11D and 11E illustrate the state of the delivery tool components after the process of discharging the ventricular function assisting device inside the left ventricle, and FIG. 11F shows the implanted device inside the left ventricle after retracting back the delivery tool;

FIGS. 12A and 12B illustrate the final steps of implanting the ventricular function assisting device of the invention inside the left ventricle, of an optional fixation element wherein FIG. 12A illustrates attaching the device to an external button, and FIG. 12B illustrates placing an apical cup externally over the apex of the heart;

FIGS. 13A to 13D schematically illustrate various techniques for deploying the ventricular function assisting device of the invention, wherein FIG. 13A illustrates using a delivery tool comprising an umbrella-like mechanism, FIG. 13B demonstrates a mechanism utilizing a balloon for opening the device, FIG. 13C demonstrates a mechanism employing wires forming basket-like shape, FIG. 13D demonstrates a mechanism employing two sets of wires;

FIGS. 15A and 15B respectively show a top view and a perspective view of a three-arms ventricular function assisting device of the invention, which arms are made in a stent-like configuration;

FIGS. 16A to 16F show perspective views of ventricular function assisting devices of the invention which arms comprise elastic slanted sections, wherein FIGS. 16A and 16B show embodiments of a three-arms device, FIGS. 16C and 16D show embodiments of three-arms devices which arms are manufactured in a stent-like configuration, FIG. 16E shows an embodiment of a four-arms device, and FIG. 16F shows a preferred embodiment of a six-arms device;

FIGS. 17A to 17C show perspective views of ventricular function assisting devices of the invention comprising a central post, wherein FIGS. 17A and 17B show a three-arms embodiment of the device which arms comprise a slanted attachment section, and FIG. 17C show an embodiment of the device which arms further comprise elastic slanted sections;

FIGS. 18A to 18E schematically illustrate embodiment of the ventricular function assisting devices of the invention using spring elements in the devices' arms, wherein FIGS. 18A and 18B respectively show a top view and a perspective view of a three-arms device which arms are attached via springs to a base section of the device, FIG. 18C shows a perspective view of an elastic arm comprising spring elements distributed along its length, FIG. 18D shows an embodiment of the elastic arm shown in FIG. 18C comprising interfacing members, and FIG. 18E shows a perspective view of a double wire embodiment of elastic arm shown in FIG. 18D;

FIGS. 19A and 19B respectively show a perspective view and a top view of three-arms embodiment of the ventricular function assisting device of the invention which arms form a spiral-star base section;

FIGS. 20A and 20B respectively show a perspective view and a top view of three-arms embodiment of the ventricular function assisting device of the invention which arms comprise a wavy portion and a portion forming a spiral-star base section;

FIGS. 21A and 21B show perspective views of ventricular function assisting devices of the invention comprising circular attachment sections, wherein FIG. 21A shows an embodiment comprising one circular attachment section, and FIG. 21B shows an embodiment comprising two circular attachment sections;

FIGS. 22A to 22E illustrate a delivery tube suitable for implanting the ventricular function assisting devices through a catheterization procedure, wherein FIGS. 22A and 22B respectively show a side sectioned view and a transparent perspective view of the delivery tube with a three-arms ventricular function assisting device of the invention comprised in its distal end section in a folded state, FIG. 22C shows a transparent perspective view of the delivery tube with the device having an anchoring helical element, FIG. 22D shows a transparent perspective view of the delivery tube with the ventricular function assisting device shown in FIG. 21B comprised in its distal end section in a folded state, FIG. 22E shows a transparent perspective view of the delivery tube with the the ventricular function assisting device shown in FIGS. 15A and 15B comprised in its distal end section in a folded state;

FIGS. 23A to 23G schematically illustrate a possible catheterization implant procedure suitable and means for implanting the ventricular function assisting devices of the invention, wherein FIGS. 23A to 23E schematically illustrate the steps of placing an anchoring element inside the heart ventricle by means of a torque wire (FIG. 23A), advancing the ventricular function assisting device towards the anchoring element (FIG. 23B), attaching the ventricular function assisting device to the anchoring element (FIG. 23C); deploying the ventricular function assisting device inside the heart ventricle, positioning of the device and removal of the delivery tube (FIG. 23D), removal of the torque wire (FIG. 23E), and wherein FIGS. 23F and 23G respectively illustrate a side sectional view and a perspective view of the torque wire and anchoring element in an engaged (FIG. 23F) and detached (FIG. 23G) states;

FIGS. 24A and 24B schematically illustrate a delivery tube suitable for implanting the ventricular function assisting devices of the invention by a single step catheterization procedure;

FIGS. 25A to 25F schematically illustrate various anchoring elements suitable for attaching the ventricular function assisting devices in catheterization approach shown in FIGS. 14 to 18 to a ventricular apex, wherein FIG. 25A illustrates an anchoring element comprising a helical/spiral anchor, FIG. 25B illustrate an anchoring element comprising fixating barbs, and FIGS. 25C to 25F illustrate a procedure of implanting an anchoring element of the invention comprising several hooks which is introduced into the myocardium through a needle;

FIGS. 26A to 26C show a simulation of an implantation procedure following the catheterization approach of the invention by means of the delivery tube shown in FIG. 16B; and, wherein FIG. 26A shows the step of attaching the ventricular function assisting device comprised inside the delivery tube in a folded state, FIG. 26B shows removal of the delivery tube, and FIG. 26C shows deployment of the ventricular function assisting device inside the heart ventricle.

Figure 1A:
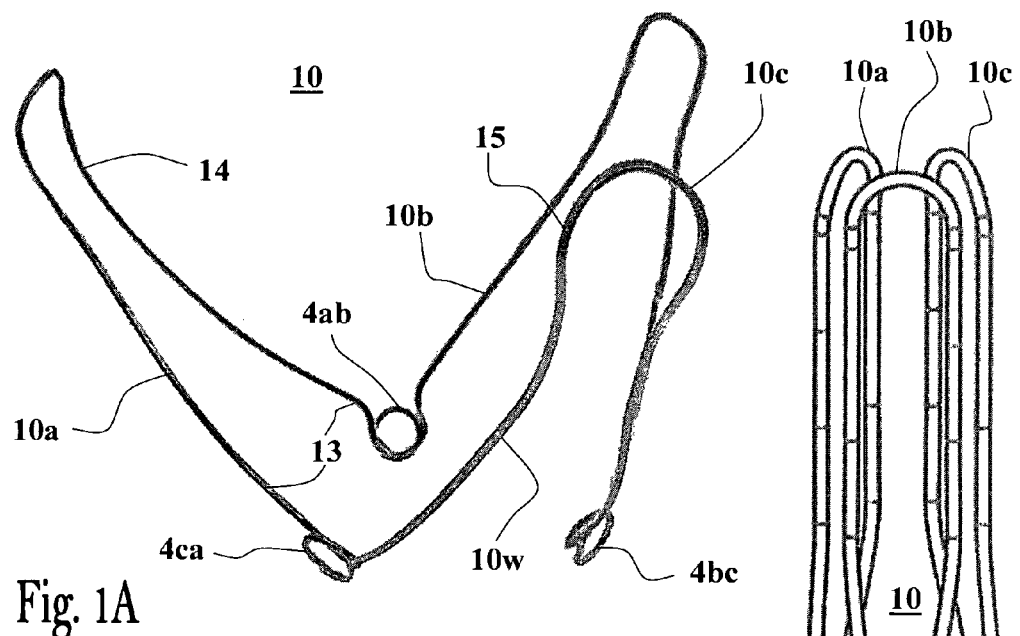

It should be noted that the embodiments exemplified in the Figs. are not intended to be in scale and are in diagram form to facilitate ease of understanding and description.

SUMMARY OF INVENTION

The present invention provides a ventricular function assisting device configured to be implanted in a heart ventricle by means of trans apical or catheterization procedures. In general, the ventricular function assisting device of the invention is designed in a form of flower-like configuration (also referred to herein as star configuration) comprising two or more petals (also referred to herein as arms) attached at a base section, said petals comprise elastic elements and/or portions capable of being elastically bent in radial directions and optionally also in sideway and/or longitudinal directions, thus allowing changing the state of the ventricular function assisting device between: i) a folded conformation, in which its petals are radially pressed inwardly towards each other to assume a reduced diameter of its flower-like configuration (i.e., a closed flower structure), thereby increasing the potential energy stored in the elastic elements and/or portions provided in the petals, such that it is capable of being placed inside a delivery tube or sheath; and ii) a deployed conformation, in which the petals are opened in a radial outward direction as the device is discharged from the delivery tube or sheath into a heart ventricle and implanted thereinside in a preloaded state such that the potential energy stored in the elastic elements or portions provided in the petals is constantly applying pressure against the walls of ventricle.

The diameter (in top view) of the ventricular function assisting device in a fully deployed state (also referred to herein as a free state i.e., when no energy is stored in the elastic elements/portions of the arms) is preferably somewhat greater than its diameter in its deployed conformation inside the heart ventricle. This configuration ascertains that the ventricular function assisting device is essentially implanted in a preloaded state (i.e., energy is stored in the elastic elements/portions of the arms).

The base section of the ventricular function assisting device may comprise a relatively thin (e.g., 0.1 to 0.7 mm) disk element comprising a central pass through bore for attaching it to the apex inside the heart ventricle, and a circumferential surface to which the bases of the petals are attached. Alternatively, the base section of the ventricular function assisting device comprises elastic torsion loops elements configured to elastically connect between bases of adjacent petals of the ventricular function assisting device, said torsion loops elements are advantageously employed to attach the ventricular function assisting device to the apex inside the heart ventricle by means of fixation suture strings passing and/or attached to the torsion loops elements.

The ventricular function assisting device may be implanted in a heart ventricle by a trans apical or a catheterization procedure. Implanting the ventricular function assisting device in a minimally invasive trans apical procedure is preferably carried out utilizing a delivery tool comprising: a delivery tube adapted to receive and hold the ventricular function assisting device in a folded state in its distal end section; and a hollow inner shaft slidably passing inside the delivery tube, said hollow inner shaft comprising a clamping mechanism adapted to releasably hold suturing string(s) attached to the base section of the ventricular function assisting device thereby allowing pushing or pulling the ventricular function assisting device placed inside the delivery tube by means of the hollow inner shaft. The trans apical implantation procedure may include the following steps:

Opening a passage to the heart apex through the patient's chest;

marking the papillary muscles for visualization by suitable marking means (radiopaque marker, tag, needle, or screwable spring);

performing a purse string at the heart apex for the insertion of a trans-apical sheath thereinto by means of a dilator;

after the dilator is removed, introducing the delivery tool into the trans-apical sheath and advancing it distally through the trans-apical sheath until the distal end of the delivery tube is introduced into the ventricle via the distal opening of the trans-apical tube;

advancing the ventricular function assisting device in a folded state through the delivery tube of delivery tool into the heart by means of the inner hollow shaft, and positioning it thereinside according to the papillary muscles marker;

manipulating the orientation of the ventricular function assisting device relative to the papillary muscles markers for properly positioning it inside the heart ventricle;

discharging the ventricular function assisting device inside the heart ventricle by distally pushing the inner hollow shaft, during which the ventricular function assisting device unfolds into a preloaded deployed state;

retracting delivery tool proximally;

retracting trans-apical sheath from the incision such that the trailing ends of the suturing string(s) threaded through the base section of the ventricular function assisting device are proximally withdrawn through the incision;

fastening the purse string to close the incision;

Suturing the incision by the purse string wires interlaced by the suturing string(s) to the apex tissue, thereby attaching the base section of the ventricular function assisting device to the bottom part of the ventricle.

In a catheterization procedure the implantation of the ventricular function assisting device of the invention may include the following steps:

Making a small incision in an artery or vein, according to the implantation route selected among either options described later on (e.g. transfemoral, axillary, subclavisn, retroperitoneal, trans-septal, or the like) by means of a needle, or any other standard equipment generally used for performing catheterization procedures for accessing into a blood vessel;

introduction through the incision a guiding tube comprising a torque wire slidably passing thereinside, wherein the distal end of the torque wire comprises an anchoring element releasably attached to it by means of a connecting mechanism;

advancing the guiding tube with the torque wire comprised in it through the vascular system of the patient into the heart ventricle by suitable visualization means Xray (e.g., fluoroscopy, angiography, ventriculography), echocardiography (e.g. trans-esophageal, trans-thoracic, intra-cardiac, 3D echo), MRI, or the like;

anchoring the anchoring element into the apex inside the ventricle;

retracting delivery tube proximally and removing it from the vascular system of the patient;

advancing a delivery tube into the ventricle over the torque wire, said delivery tube comprising a flexible distal section and the device placed inside the distal end portion thereof until the delivery tube reaches the anchoring element;

attaching the base section of the ventricular function assisting device to the anchoring element;

manipulating the orientation of the ventricular function assisting device according to the internal anatomy of the ventricle to properly place it thereinside;

retracting proximally and removing the delivery tube thereby discharging the ventricular function assisting device such that its arms are pressed against the inner walls of ventricle in a preloaded state (i.e., with some energy stored in the elastic elements/portions provided in the arms);

inserting a delivery catheter into the ventricle, said delivery catheter comprising a securing element;

attaching the securing element to the anchoring element;

releasing the attachment of the torque wire to the anchoring element and removing it from the patient's body.

According to one aspect the present invention is directed to a ventricular function assisting device comprising two or more arms each of which comprising a bottom end, a free top end and an intermediate section extending between said ends, wherein said bottom ends of said two or more arms are attached in a base section of said device thereby forming a flower cup configuration, and wherein said two or more arms comprise elastic elements or portions configured such that they are capable of being elastically bent in radial directions relative to longitudinal axis of said flower cup configuration, and wherein said device is capable of being set into at least two conformations: i) a folded conformation, in which said two or more arms are pressed inwardly in a radial direction towards each other thus allowing fitting it in a delivery tube or sheath in said folded conformation; and ii) a deployed conformation, in which said two or more arms are opened in a radial outward direction, wherein said device is adapted to be attached at its base section to an apex inside a heart ventricle in said deployed conformation such that at least its free top ends are pressed against the walls of said heart ventricle thereby allowing said two or more arms to elastically bent in radial directions during contractions of said heart ventricle, and thereby store potential energy in said elastic elements or portions provided thereof, and to release said energy during expansions of said heart ventricle.

Portions of the arms of the ventricular function assisting device, or their entire length, or the whole ventricular function assisting device, may be adapted to be pressed against the wall of the heart ventricle, preferably in a preloaded state such that some energy is stored in the elastic elements/portions provided in the arms in its deployed state inside the heart ventricle.

Optionally, portions of the arms, or their entire surfaces, are covered by a padding element, said padding element is preferably adapted to promote tissue ingrowth. Alternatively or additionally, portions of the arms may comprise apertures adapted to promote tissue ingrowth. Advantageously, the padding element may be adapted to release a drug into the tissue of the heart. Additionally, portions of the arms, or their entire area, may be covered by a layer of material suitable for promoting tissue growth and/or with hemocompatible coating.

Advantageously, the two or more arms may be adapted to elastically bend in sideway directions in response to twist movements and longitudinal movements of the heart ventricle in which it is implanted.

The base section of the ventricular function assisting device may comprise a disk element comprising a central pass through bore adapted for attaching it to the apex inside the heart ventricle, and a circumferential surface to which the bases of the one or more arms are attached.

The base sections of the ventricular function assisting device may comprise elastic torsion loops elements configured to elastically connect the bottom ends of adjacent arms of said ventricular function assisting device, wherein said torsion loops are further employed to attach said ventricular function assisting device to the apex inside the heart ventricle by means of suture strings passing through and/or attached to said torsion loops elements. The base section of the ventricular function assisting device may comprise a cup shaped element having an attachment bore provided in its base and a circumferential surface to which the arms of said ventricular function assisting device are attached.

The arms of the ventricular function assisting device may be manufactured to form an elastic mesh having rhombus, or other geometry, shaped apertures. Alternatively, the ventricular function assisting device may be manufactured from an elastic wire or from a layered structure of elastic strips.

The arms of the ventricular function assisting device may further comprise elastic corrugations formed along their lengths, in their free top end, and/or in their bottom ends.

Advantageously, the arms of the ventricular function assisting device may comprise one or more bent sections for improving their flexibility.

The arms of the ventricular function assisting device may be attached to the base section by means of springs. Additionally or alternatively, the arms of the ventricular function assisting device may comprise one or more springs provided along their lengths for improving their flexibility.

In one specific embodiment the bottom sections of the arms of said ventricular function assisting device are curved such that a spiral star structure is formed in the base section.

According to another embodiment the ventricular function assisting device comprises one or more elastic circular attachment sections attached by means of a connecting strip the base section of the device, said base section comprising a pass through attachment bore for attaching the device to an anchoring element in a ventricle of the heart, wherein the elastic circular attachment sections are adapted to be mounted inside the heart ventricle such that their outer surface is pressed against the heart tissue. The elastic circular attachment sections may comprise a plurality of apertures distributed over their surfaces for promoting tissue ingrowth and adhesion. The elastic circular attachment sections are preferably designed to be rolled to allow placing the device inside a delivery tube such that when the device is discharged from said delivery tube inside the heart ventricle the rolled elastic circular attachment sections open and become pressed over a circular sector (e.g., 90 to 350 degrees) of the wall of the ventricle.

According to another aspect the present invention is directed to a method for implanting the ventricular function assisting device by a trans apical or catheterization procedure, as described hereinabove and hereinbelow.

According to yet another aspect the present invention is directed to a delivery tool, as described hereinabove and herein below, for delivering and implanting the ventricular function assisting device of the invention by a trans apical procedure.

The present invention is also directed to a delivery system, suitable for implanting the ventricular function assisting devices of the invention by a single step, or multi steps, catheterization procedure, said delivery system comprising a delivery tube comprising: a proximal handle adapted for steering, turning, pushing and pulling the delivery tube, wherein the distal section of the delivery tube is made flexible and have a tapering tip configured to receive said ventricular function assisting device in a folded state (i.e., wherein the elastic arms of the device are pressed toward each other); a torque tube passing inside delivery tube along its length, said torque tube is made in a form of a hollow tube; a guidewire slidably passing inside the torque tube; and an anchoring element releasably attached to torque tube, said anchoring element comprising a waist section adapted to receive the base section of said ventricular function assisting device, a distally attached helical or spiral anchor, and an internal passage provided along its length being such that the guide wire may be passed through the internal passage of the anchoring element.

A possible implantation procedure utilizing this delivery system may include the following steps:
  making a small incision in an artery or vein as described hereinabove and introducing the guidewire through the vascular system into the heart ventricle;
  fitting a ventricular function assisting device of the invention over the waist section provided in the anchoring element;
  advancing the delivery tube comprising the torque tube, the anchoring element, and the ventricular function assisting device in its flexible distal portion, via the vascular system over the guide wire into the treated heart ventricle;
  advancing the helical or spiral anchor outside of delivery tube via it tapered end tip by pushing torque tube distally;
  screwing helical or spiral anchor into the heart tissue by turning of the torque tube via its handle;
  adjusting the orientation of the ventricular function assisting device according to the internal anatomy of the ventricle by manipulating delivery tube;
  discharging the ventricular function assisting device by retracting delivery tube proximally such that its arms change into a deployed preloaded conformation as they become pressed against the internal walls of the ventricle;
  retracting distally the delivery tube;
  releasing the attachment between the torque tube and the anchoring element; and
  retracting proximally the delivery tube with the torque tube and guidewire inside it.

DETAILED DESCRIPTION OF PREFERRED EMBODIMENTS

The present invention provides a ventricular function assisting device configured to be implanted in one of the ventricles of the heart preferably in the left ventricle of a DHF heart. After implanting the device inside the ventricle it stores energy, originated from the heart motion, taken from the myocardium movement during the systole, and releases the energy stored in it during the diastole, thereby augmenting diastolic performance of the heart. More particularly, the ventricular function assisting device of the invention generally comprises two or more "arms" connected to each other at one end, wherein said arms are made from an elastic material, or comprise elastic elements, and the device is implanted in a ventricle in a preloaded state (i.e., the diameter of the device outside of the heart ventricle in a top view perspective when its arms are in a fully deployed state is greater than the diameter of the ventricle). Thus, additional elastic potential energy is stored in the bent arms of the device during the systole, as the arms are further pressed radially inward by the wall of the heart toward each other, whereas in diastole, as the ventricle walls are expanded and the arms of the device move radially outward, the elastic potential energy stored therein is released, while said preload ensures that the device is continuously loaded with elastic potential energy until the end of the diastolic phase, thereby available for diastolic performance augmentation.

According to one preferred embodiment of the invention the ventricular function assisting device is implanted inside a left ventricle such that the part where its arms are connected (also referred to as base area herein) is placed inside the ventricle at the apex of the heart, on the endocardial surface, and its arms are bent upwardly relative to said base points such that the arms rest on the inner walls of the ventricle. In this way, the arms of the ventricular function assisting device are forced to bend toward each other during heart systole, and thereby store potential energy, due to their elasticity. Correspondingly, during heart diastole the potential energy stored in the arms of the device is converted into kinetic energy as said arms push the walls of the ventricle radially outward and thereby assist in heart expansion. The arms of the ventricular function assisting device preferably have a round and curved shape such that they fit the left ventricle shape and rest on the inner walls of the ventricle. The vertices of the arms of the device are preferably curved and rounded in order to provide a smooth and safe implantation of the device on the endocard, and for preventing them from being caught in the tissue of the inner walls of the ventricle. Additionally, the vertices of the arms may comprise elastic corrugations and/or elastic elements embedded therein for allowing them the flexibility to be loaded with energy taken from movement of the walls of the heart ventricle in radial and/or sideway and/or longitudinal directions in response to contraction, expansions, circumferential twists and longitudinal motions of the heart.

FIG. 1A shows a preferred embodiment of the ventricular function assisting device 10 of the invention comprising three arms, 10a, 10b and 10c. In this preferred embodiment ventricular function assisting device 10 is made from an elastic wire 10w formed in a shape of a three-arms star. The elastic wire 10w is shaped such that three loops, 4ab, 4bc and 4ca, are wound at the connections of the base points connecting arms 10a, 10b and 10c. Suturing string (e.g., 5 shown in FIG. 2A) are preferably passed through loops 4ab, 4bc and 4ca, for fixation by suturing the device inside the ventricle, and for folding and retracting back the device inside the delivery tool (shown in FIG. 11A) used in the implantation process of the device. The device 10 can be also attached to the heart tissue by small hooks, needles or screws, for example.

In the ventricular function assisting device exemplified in FIG. 1A each of the arms 10a, 10b and 10c, comprises a relatively wide waist section 13 near the base area comprising loops, 4ab, 4bc and 4ca, and the width of the arms is gradually decreased towards a relatively narrow neck section 14 located near their rounded vertices, such that a head section 15 is formed at the apexes of the arms.

Figure 1B:
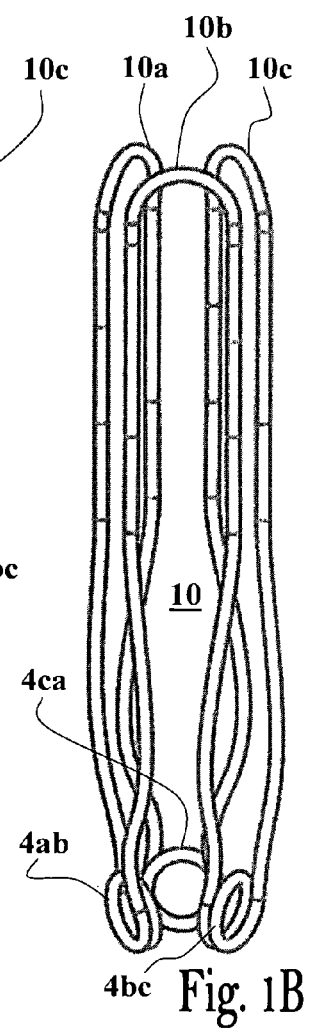

The ventricular function assisting device 10 shown in FIG. 1A is in a free state, namely, no potential energy is stored in the device at this state. FIG. 1B illustrates the ventricular function assisting device 10 of the invention in a folded state, wherein the arms of the device are pressed toward each other for introducing it into the delivery tool (shown in FIGS. 11A-C).

Ventricular function assisting device 10 may be made from any biocompatible material suitable for implementing an elastic wire, such for example stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The ventricular function assisting device may be manufactured from a radiopaque material, or alternatively, it may comprise radiopaque markers. The diameter of the elastic wire of the ventricular function assisting device may generally be in the range of 0.2 to 1 mm. The length of each arm 10a 10b 10c may generally be in the range of 25 to 60 mm, preferably about 45 mm. The width at waist section 13 of the arms may generally be in the range of 10 to 20 mm, preferably about 15 mm, and at the neck section 14 generally in the range of 4 to 10 mm, preferably about 6 mm. The upper diameter encircling the device in top view when in a fully deployed state (free state) may generally be in the range of 40 to 90 mm and its lower diameter in the same conditions may generally be in the range of 15 to 50 mm. It is however noted that the parameters defined above may vary depending on the dimensions of the heart to be treated.

Figure 2A:
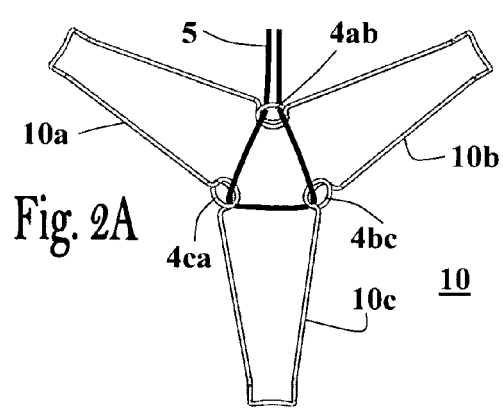
FIGS. 2A to 2C show various ways for attaching a fixation suture string to the three arm of the ventricular function assisting device of the invention, wherein in FIG. 2A a single suture string is threaded through the base point loops, in FIG. 2B a suture string is threaded through each pair of neighboring loops, and in FIG. 2C a suture string is attached to each loop.
Figure 2B:
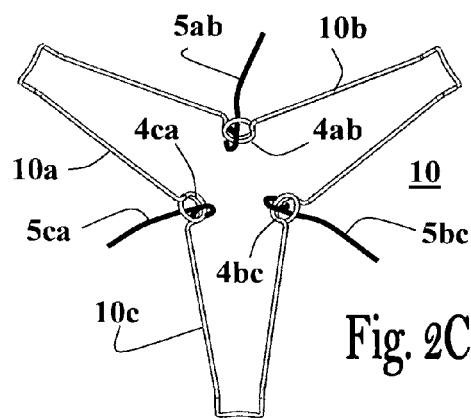
Figure 2C:
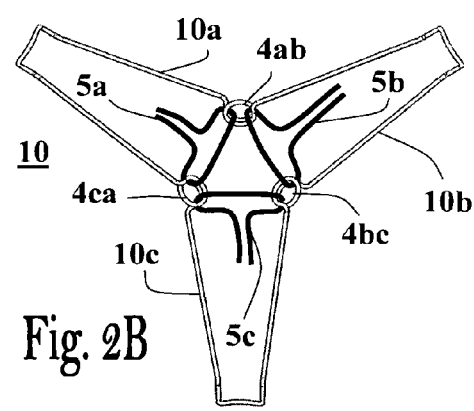

As demonstrated in FIGS. 2A to 2C, a fixation suture string (5) can be attached to the ventricular function assisting device 10 in various ways. FIG. 2A illustrates an example wherein a single suture string 5 is threaded through the base loops, such that it is passed circularly through the base loops 4ab, 4bc and 4ca, formed at the bases of the arms. In this example string 5 introduced through loop 4ac, passes through base loops 4ab and 4bc, and then passed again through base loop 4ac. In FIG. 2B separate suture strings, 5a, 5b and 5c, are threaded through corresponding pairs of neighboring base loops, (4ca and 4ab), (4ab and 4bc) and (4bc and 4ca). In the example shown in FIG. 2C separate suture strings, 5ab, 5bc and 5ca, are attached to corresponding base loops, 4ab, 4bc and 4ca.

FIGS. 3A and 3B show perspective views of two preferred embodiment wherein the ventricular function assisting device 10 of the invention further comprise padding covering portions of the device, or its entirety. FIG. 3A shows a preferred embodiment wherein end vertices sections of the arms, 10a, 10b and 10c, of device 10 comprise corresponding padding elements, 8a, 8b and 8c. The padding elements may be made from a biocompatible fabric configured to partly or totally cover the device's arms or even cover the whole device. For example, padding elements 8a, 8b and 8c, may comprise a grid or a fabric/polymeric in a knit, braid, or woven structure. Preferably, padding elements 8a, 8b and 8c, are made from PET, synthetic or biological polymer, and/or from other suitable biocompatible fabric materials, stretched over end vertex sections of the arms' of device 10 for promoting tissue growth and adhesion thereof to the heart tissue. The adhesion of padding elements, 8a, 8b and 8c, by tissue ingrowth to the heart tissue assists in distributing the forces applied by the arms of the device over the heart tissue, and in preventing penetration of the tips of the arms into the heart tissue. Of course, other suitable materials and designs may be used for the padding elements.

FIG. 3B shows an embodiment 60 wherein the entire device (10) is covered with a padding element 61 made from a biocompatible material suitable for promoting tissue ingrowth and adhesion as discussed above. In this preferred embodiment the padding element 61 comprises inverted "V"-shaped sleeves 60a 60b 60c designed to enclose the arms (10a 10b 10c) of the ventricular function assisting device of the invention, and corresponding base pockets 1ab 1bc 1ca designed to enclose the torsion base loops of the device (4ab 4bc 4ca).

FIGS. 4A to 4D show a preferred embodiment of a three-arms ventricular function assisting device 11 of the invention having torsion loops 4ab 4bc 4ca at the base of the arms, and vertex torsion loops 7a 7b 7c provided in the vertex of each of the arms 11a 11b 11c. FIG. 4A shows a perspective view of device 11 and FIG. 4B shows a top transparent view of device 11 encased inside a padding cover 12. Padding cover 12 comprises inverted "V"-shaped sleeves designed to enclose arms 11a 11b 11c of device 11 and their vertex torsion loops 7a 7b 7c, and corresponding base pockets 6ab 6bc 6ca designed to enclose the torsion base loops 4ab 4bc 4ca of device 11. FIGS. 4C and 4D respectively show a perspective view and a top view of device 11 encased in padding cover 12 further comprising fixation suture strings 9ab 9bc 9ca attached to the base torsion loops (4ab 4bc 4ca seen in FIG. 4B) through the padding cover 12 or attached to the padding cover 12 near the base torsion loops at the bottom of the base pockets 6ab 6bc 6ca.

Figures 5A, 5B, 5C, 5D:
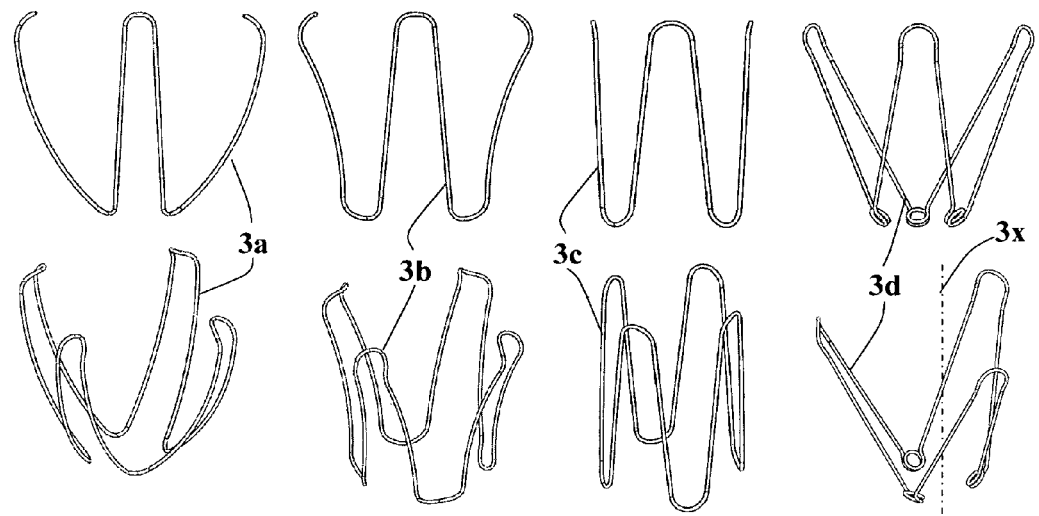

Ventricular function assisting device 10 or 11 can be designed in different shapes suitable for fitting to the left ventricle morphology, as demonstrated in FIGS. 5A to 5D, with different number of arms, with different arm shapes and lengths, with different enclosing diameters at the upper (vertex) and lower (base) loops, and with different numbers and diameters of loops at the arms vertex and at the base area of the devices. FIG. 5A shows side and perspective views of a rounded four-arms configuration 3a of the ventricular function assisting device of the invention, in which the arms are curved outwardly. FIG. 5B shows side and perspective views of a four-arms configuration 3b in which the arms are curved inwardly. FIG. 5C shows side and perspective views of a four-arms configuration 3c in which the arms are relatively straight. FIG. 5D shows side and perspective views of a three-arms configuration 3d having relatively straight arms, wherein said arms are slanted relative to a longitudinal axis 3x of the device and comprise one or more base torsion loops formed from wire loops/turns.

Figures 6A, 6B, 6C:
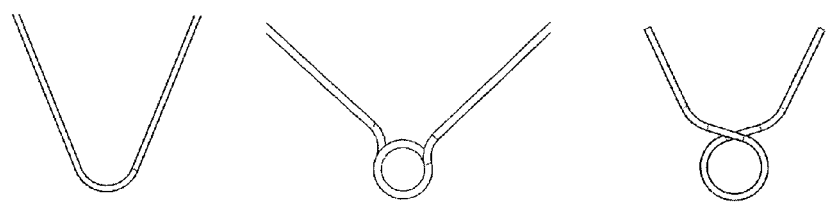

FIGS. 6A to 6C illustrate preferred configurations of the arms base sections, wherein FIG. 6A shows a base point configuration made without loops, FIG. 6B shows a base point configuration comprising one or more torsion loops, and FIG. 6C shows a base point configuration comprising a single-turn (crossed) loop.

Figure 7A:
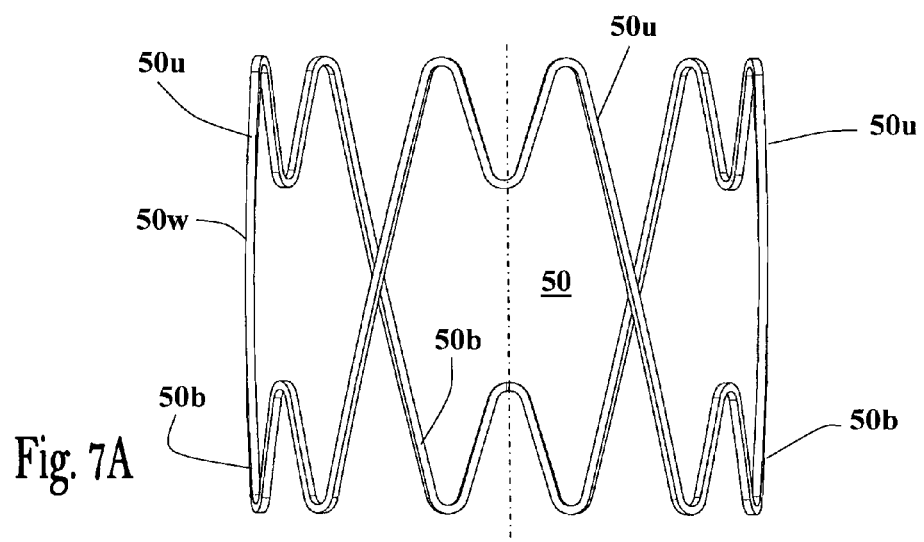

The ventricular function assisting device of the invention may be produced by means of laser cutting, as exemplified in FIGS. 7A to 7F. FIGS. 7A and 7B respectively show side and perspective views of a ventricular function assisting device 50 of the invention comprising elastic corrugations wherein the vertex sections 50u of the arms are configured in a "M"-like shape, and the base section 50b connecting said arms are configured in a "W"-like shape. This "M"-like and "W"-like curve shaping of the vertex and base areas of the arms of device 50 is designed to reduce stresses which may develop at those areas during operation of the ventricular function assisting device, when implanted inside a ventricle. Of course, vertex sections 50u and base sections 50b may be configured to comprise additional elastic corrugations for adding more flexibility in these areas of the device. FIG. 7C shows a perspective view of a specific embodiment 53 wherein the arms further comprise "Ω"-like shaped torsion sections 55 for adding flexibility in sideway directions, thus further reducing stresses that may develop over the arms during device operation, particularly stresses related to the ventricular twist and longitudinal motion.

Ventricular function assisting devices 50 and 53 may be manufactured by laser cutting techniques, such that it may be cut from a tube made for example from stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The diameter of devices 50 and 53 in top view when in a fully deployed state (free state) may generally be in the range of 40 to 90 mm, preferably about 65 mm, and the thickness of the cut material may generally be in the range of 0.4 to 1.5 mm, preferably about 0.8 mm. In this way, the laser cutting the tube (not shown) in the desired shape produce rectangular cross section wires, 50w and 53w, from which devices 50 and 53 are respectively formed. The geometric dimensions of rectangular cross section wires 50w and 53w of ventricular function assisting devices 50 and 53 may generally be in the range of 0.4×0.4 to 1.5×1 mm, preferably about 0.5×0.5 mm.

FIGS. 7D to 7F illustrate another specific embodiment 51 wherein the arms of the device are made from a multi layered strip. Similarly, device 51 can be manufactured by means of laser cutting techniques, and it is similarly designed with "M"-like and "W"-like curve shaping of the vertex (51u) and base (51b) areas of the arms. As best seen in FIG. 7E, showing a close-up of vertex 51u of an arm in multi layered strip configuration device 51, in this example the arms are cut to comprise three layers which are interconnected at the central vertex points 51t of the "M"-like and "W"-like curved sections. FIG. 7F shows the multi layered strip device 51 in a folded conformation.

The multi layered strip device 51 is mainly designed to reduce the stresses that may develop while maintaining the applied forces in the rectangular cross section of ventricular function assisting devices 50 and 53. Multi layered strip device 51 may be manufactured by laser cutting techniques, such that it may be cut from a tube made for example from stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The diameter of multi layered strip device 51 in top view when in a deployed state may generally be in the range of 40 to 90 mm, preferably about 65 mm, and the overall thickness of its layered structure may generally be in the range of 0.4 to 1.5 mm, preferably about 0.8 mm. In this specific embodiment, the laser cutting the tube (not shown) in the desired shape produce three adjacent elongated strips 51s (shown in FIG. 7E) forming the layered strip of device 51. The geometric dimensions of each strip 51s in ventricular function assisting device 51 may generally be in the range of 0.4×0.1 to 1.5×0.4 mm, preferably about 0.8×0.2 mm, and the gap between such adjacent strips 51s is preferably about 0.1 to 0.4 mm.

Figure 8D:
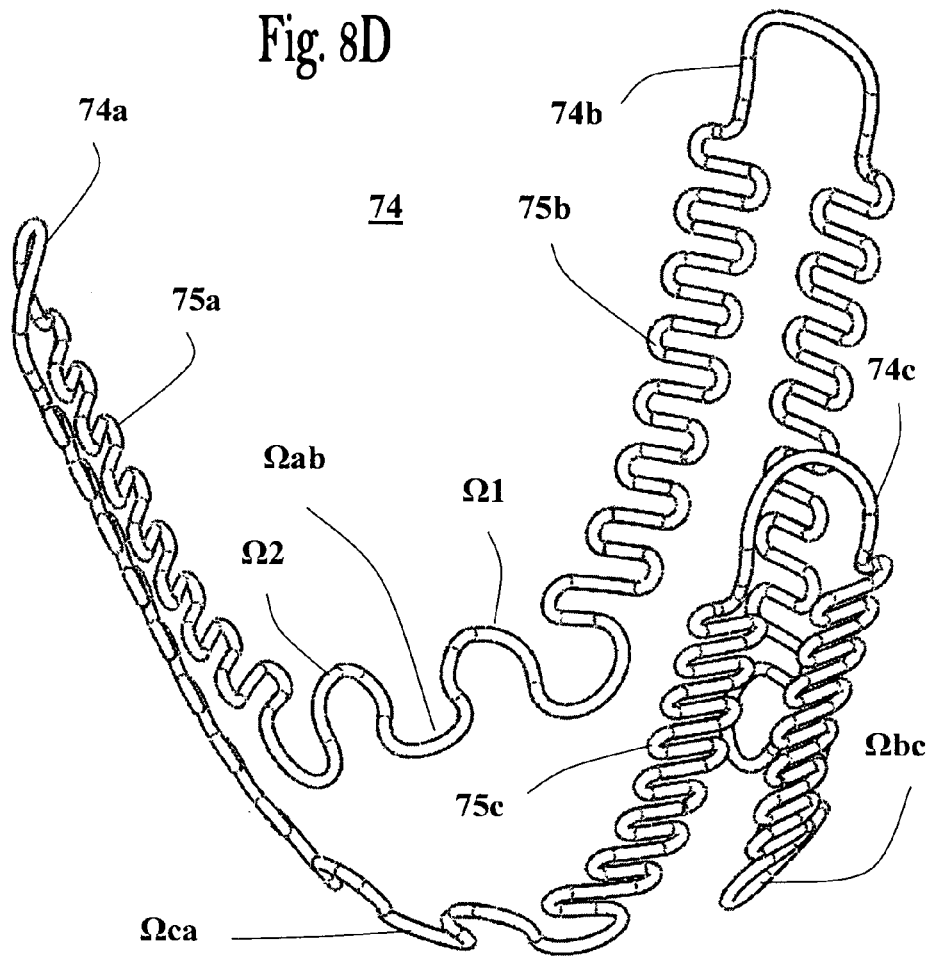

FIGS. 8A to 8E demonstrate specific embodiments of three-arms ventricular function assisting devices of the invention configured to comprise means for reducing operation stresses which may develop over the arms of the devices. FIG. 8A schematically illustrates an embodiment of the arms (e.g., 10a, 10b and 10c in FIG. 1A) of the ventricular function assisting device of the invention comprising corrugated (wavy) sections 10s designed for assisting in the longitudinal contraction of the arms.

FIG. 8B shows a specific embodiment 70 of the three-arms ventricular function assisting device of the invention comprising base torsion loops 7ab 7bc 7ca, wherein the upper section of the arms 70a 70b 70c comprise corresponding elastic corrugated sections 71a 71b 71c. More particularly, in each inverted "V"-shaped arm (70) a pair of sinusoidal-shape corrugated sections (71) are formed at the upper portion of the arm, said pair of sinusoidal-shape corrugated sections (71) are formed in the plane of the arm and preferably being symmetric relative to the longitudinal axis of the arm (not shown). In this example each corrugated sections (71) is made to consist of two consecutive sinusoidal patterns designed to absorb forces applied along the longitudinal direction of the arms.

FIG. 8C shows another specific embodiment 72 of the three-arms ventricular function assisting device of the invention comprising base torsion loops 7ab 7bc 7ca, wherein the arms 72a 72b 72c comprise corresponding pairs of elastic corrugated sections 73a 73b 73c formed along a substantial portions of their lengths. Similarly, each inverted "V"-shaped arm (72) comprise a pair of sinusoidal-shape corrugated sections (73) formed in the plane of the arm and which are preferably being symmetric relative to the longitudinal axis of the arm (not shown). In this example each corrugated sections (71) is made to consist of 4.5 consecutive sinusoidal patterns. Of course other wavy patterns having more or less corrugations are also possible. This specific embodiment is designed to absorb forces applied along the longitudinal direction of the arms and also to allow the arms to elastically bend in sideway directions responsive to heart circumferential twists occurring during its operation.

FIG. 8D shows another specific embodiment 74 of the three-arms ventricular function assisting device of the invention wherein the arms 74a 74b 74c of device 74 are formed from elastic corrugations 75a 75b 75c formed along the entire length of the arms, and wherein arms 74a 74b 74c are connected at the base area of device 74 by means of corresponding cascaded "Ω"-like shaped torsion sections Ωab Ωbc Ωca. Similarly, the corrugations (75) formed in each arm comprise a pair of sinusoidal-shape corrugated sections (75) formed in the plane of the arm and which are preferably being symmetric relative to the longitudinal axis of the arm (not shown). In this example the corrugations (75) consist of 7.5 (not obligating) consecutive sinusoidal patterns, but of course other wavy configurations comprising more, or less, elastic corrugations may be equally used. This specific embodiment is also designed to absorb forces applied along the longitudinal direction of the arms and to elastically bend in sideway directions responsive to heart twist movements.

Figure 8E:
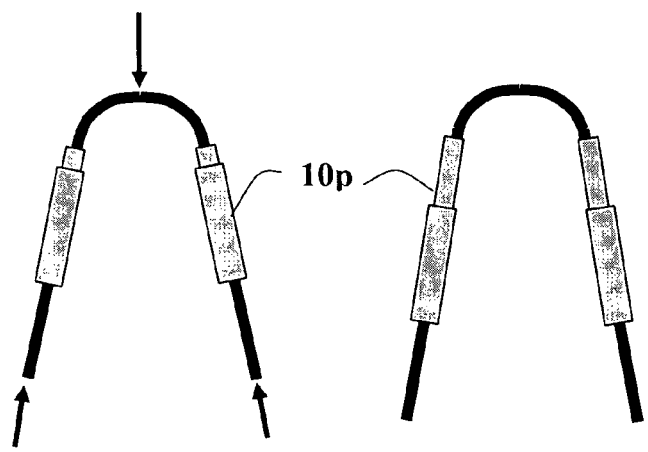

FIG. 8E schematically illustrates an embodiment of the arms of the ventricular function assisting device comprising pistons 10p designed for absorbing longitudinal movement of the heart.

Figure 9A:
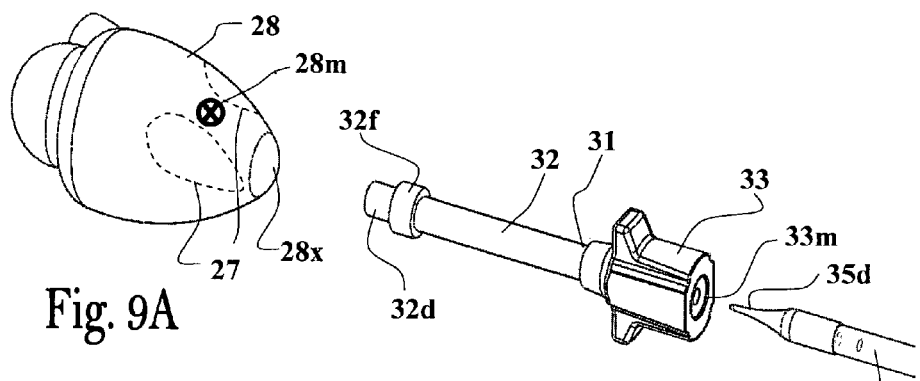

The ventricular function assisting device of the invention is intended for on-pump, or off-pump, beating heart implantation after left thoracotomy or open chest surgery or minimal invasive procedure (for trans-apical implantation procedure), or catheterization (for example, but not limited to, for Aortic retrograde, subclavian, axillary, retroperitoneal approaches or Antegrade femoral venous route) performed by cardiac surgeons or interventional cardiologist. With reference to FIGS. 9A, 9B, 10A, 10B, 11A to 11F and 13A to 13D the implantation procedure of the ventricular function assisting device of the invention by a trans-apical approach, may be performed as follows:

Initially, the papillary muscles (PM) 27 (as shown in FIG. 9A) boundaries are marked for visualization by means of standard imaging methods (e.g., X-ray, TEE, U.S etc) or with external marker 28m, generally a radiopaque marker, tag, or needle, preferably by means of a spring made of a stainless steel alloys, or a type of super alloy (e.g., 35N LT, MP35N, L605 etc.), preferably from FWM1058 alloy. The PM marker 28m having a length generally in the range of 3 to 9 mm, preferably about 7 mm, an outer diameter generally in the range of 3 to 6 mm, preferably about 4.2 mm and a pitch generally in the range of 1 to 3 mm, preferably 2 mm. The PM marker 28m is placed externally to the left ventricle, screwed into the heart tissue 28, at the gap between the papillary muscles 27. PM marker 28m is then utilized under echocardiography guidance for aiding the implantation process and placing the device in a proper location inside heart 28; The PM marker can be removed post device implantation. The PM can be also marked through an internal marker by a catheterization procedure (e.g. contrast media injection). The device guidance in relation to the PM location can be performed through imaging modalities (e.g. Trans Esophageal Echo, Intra Cardiac Echocardiography etc.).

Figure 10A:
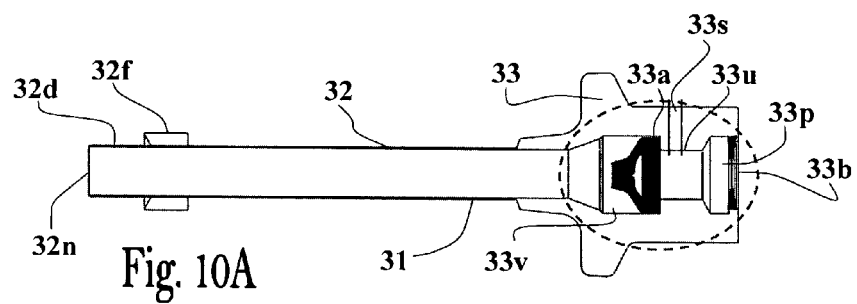
FIGS. 10A and 10B show longitudinal-section views of the trans apical sheath of the invention used for in the trans apical procedure, before (FIG. 10A) and after (FIG. 10B) introducing the dilator thereinto.
Figure 10B:
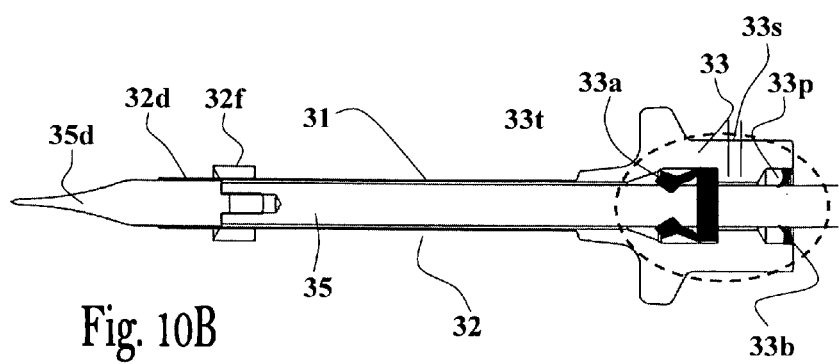

A purse string is then performed at the heart apex 28x for the insertion of a trans-apical sheath 31 thereinto by means of a dilator 35, in order to set a route for the insertion of the distal section 32d of the trans-apical tube 32 into the heart 28 through a small dissection 28a located at the middle of the purse string (The trans-apical sheath 31 is washed prior to the insertion, generally with saline solution, preferably with saline and heparin, introduced thereinto through a washing port (33s, shown in FIGS. 10A-10B);

After the purse string is performed, dilator 35 is retracted backwardly out from the trans-apical sheath 31;

As demonstrated in FIG. 11A, the delivery tube 22 of delivery tool 30 is then introduced into trans-apical sheath 31, after being washed generally with saline, preferably with saline and heparin introduced thereinto through inlet 38. The delivery tool 30 is then advanced distally through trans-apical sheath 31 until the distal end 22d of delivery tube 22 is introduced into the ventricle via the distal opening 32n of tube 32 of trans-apical tube 31;

Ventricular function assisting device 10 is then advanced in a folded state (shown in FIGS. 11A and 11B) through the delivery tube 22 of delivery tool 30 into the heart 28, and positioned thereinside according to the PM marker 28m, or any other method used for marking and/or observing the PM (e.g., any suitable imaging modality such as TEE). Proper positioning of device 10 inside the heart 28 may be achieved by placing ventricular function assisting device 10 inside trans-apical sheath 32 such that one of its arms is aligned with the clamp 34s provided on delivery tool's handle 34h. In this way the device 10 can be advanced and discharged out of the delivery tool 30 into a proper position inside ventricle 28, by maintaining a straight line between the external marker 28m and clamping means 34s. In other words, the location of the device's arm to be placed between the papillary muscles 27 is represented by the clamping means 34s passing through the delivery tool's handle 34h.

After ventricular function assisting device 10 is released inside heart ventricle 28, during which it unfolds into a preloaded deployed state (shown in FIG. 11E), the delivery tool is retracted out. Thereafter the trans-apical sheath 32 is slowly retracted out from incision 28a such that the trailing ends of the fixation suturing string threaded through the base points of the device arms are withdrawn externally to the heart through incision 28a and the purse string is immediately fastened to close the incision 28a;

Incision 28a is then sutured by the purse string wires interlaced by the suturing string wires 5 to the apex tissue, thereby attaching the loops, of the ventricular function assisting device 10 to the bottom part of the ventricle.

FIG. 11B schematically illustrates the implantation of ventricular function assisting device 10 in heart ventricle 28, by means of the delivery tool 30 of the invention. As shown, device 10 is introduced via incision 28a made at the apex (28x FIG. 9A) of heart 28. Device 10 is shown in FIG. 11D in its deployed state after being delivered into the heart 28 through delivery tube 22 of delivery tool 30. In its folded state (shown in FIGS. 11A-11C), the arms of device 10 are closely held together so that the diameter of device 10 is reduced to about 7 mm, which allows sliding it through tube 22.

With reference to the sectional view shown in FIG. 10A, trans apical sheath 31 generally comprises a distal tube 32 communicated with a proximal hollow connector element 33, comprising a distal seal 33a, which completely seals the trans-apical sheath 31 when it is closed (i.e., before introducing any additional device into the trans apical sheath), and a proximal seal 33b having a centralized hole for the insertion and seal around the dilator 35, or around the delivery tool 30, which are introduced thereinto during the procedure and change distal seal 33a into an opened state.

FIG. 10B shows a sectional view of trans-apical sheath 31 with dilator 35 passing distally thereinside via proximal and distal seals, 33b and 33a, and via tube 32. The distal tip 35d of dilator 35 comprises a graded diameter designed to allow the surgeon to dilate incision 28a. The dilator 35 is introduced into trans-apical sheath 31 via proximal opening 33p of hollow connector 33, and passed therethrough until its distal end 35d emerges via the distal opening of tube 32.

Figure 9B:
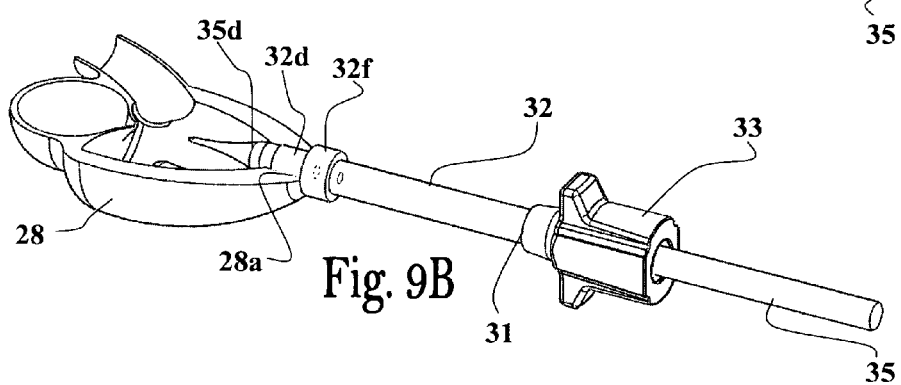

As best seen in FIG. 9B, distal portion 32d of trans-apical tube 32 and distal end 35d of dilator 35 are introduced into heart 28 via incision 28a until flange stopper 32f at the distal end 32d abuts the wall of heart 28. With reference to FIG.

10B, in this state distal seal 33a is fully opened and thus significant portions of the blood pressure are exerted over proximal seal 33b. On the other hand, as seen in FIG. 10A, when dilator 35 is removed from trans-apical sheath 31, the distal seal 33a is closed and thus blood pressure is entirely exerted over distal seal 33a. In this way, the distal ends 35d of dilator 35 and 32d of tube 32, may be introduced via incision 28a, and dilator 35 may be removed, while leaving tube 32 attached to heart 28 and preventing blood loss.

The delivery tool is inserted into the trans-apical sheath 31 after being washed generally with saline, preferably with saline and heparin through the fluid inlet 38. When the delivery tool is introduced into the trans-apical sheath 31 device 10 is folded and placed at the distal part of the trans-apical sheath (possible with crimper device—not shown) as shown in FIGS. 11A and 11B. A mechanism of a linear movement 34 comprising a movable handle 34h operated by a motor (not shown) or manual screwing mechanism and clamping means 34s are then distally progressed to release the device 10 from the delivery tool 30 into the heart 28 by pushing distally the inner (hollow) shaft 39, as shown in FIG. 11C-11D. The trailing ends of fixation suture string 5 passing, through and along the delivery tool 31, are clamped and sealed around by clamping means 34s provided in handle 34h. As shown in FIG. 11D, distal seal 40 is placed around the fixation suture strings 5 for preventing blood leakage from the inner shaft 39 around the suture strings 5, and proximal seal 41 is placed around the inner shaft 39, for preventing blood leakage form the distal tube 32 around the inner shaft 39. Handle 34h may be retracted backwardly (proximally) for inserting ventricular function assisting device 10 back into trans-apical tube 32 for its relocation, if needed. After ventricular function assisting device 10 is released inside the heart ventricle, as shown in FIG. 11D, the fixation suture string 5 is discarded from the holding of clamping means 34s, and it is then interlaced with the purse string wire 52 to the apex, as shown in FIG. 11F.

Both the trans-apical sheath 31 and the delivery tool 30 can be made of a biocompatible material for short term use such as metal or plastic, and may be combined with radiopaque markers.

Trans-apical tube 32 may be made from a biocompatible material for short term use such as metal or plastic, preferably from PC or Stainless Steel, having a length generally in the range of 50 to 150 mm, preferably about 90 mm, and its outer diameter may be generally in the range of 6 to 15 mm, preferably about 8.3 mm, and its inner diameter may be generally in the range of 5 to 14 mm, preferably about 8 mm.

The Delivery Tool 30 may be made from a type of biocompatible material for short term use, such as, stainless steel, for example, or stainless steel 303, its length may generally be in the range of 150 to 350 mm, preferably about 250 mm, its outer diameter may generally be in the range of 5 to 14 mm, preferably about 8 mm and its inner diameter may generally be in the range of 4 to 14 mm, preferably about 7.3 mm. The washing tube 38 may be made from a type of biocompatible plastic or PC for short term use.

Figure 12A:
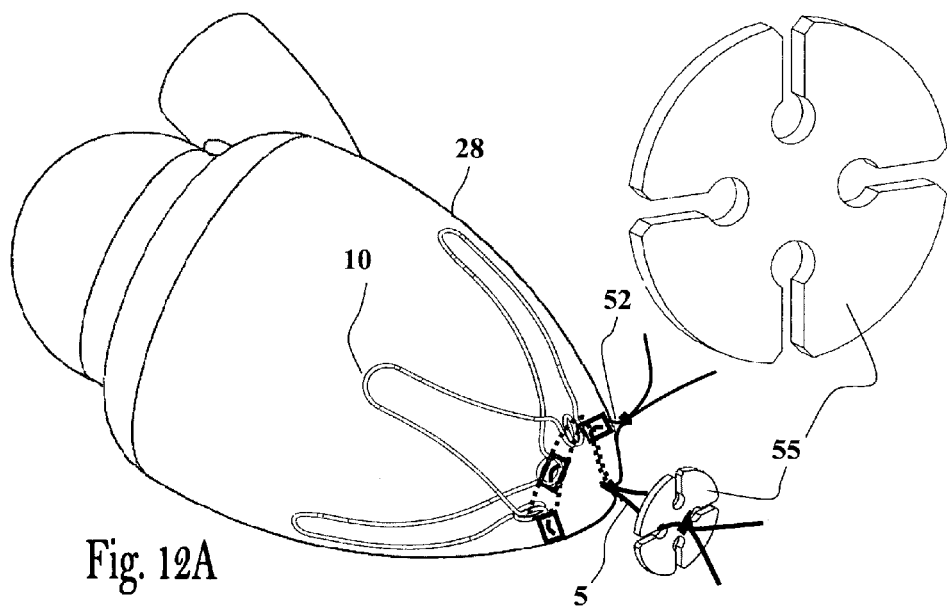
Figure 12B:
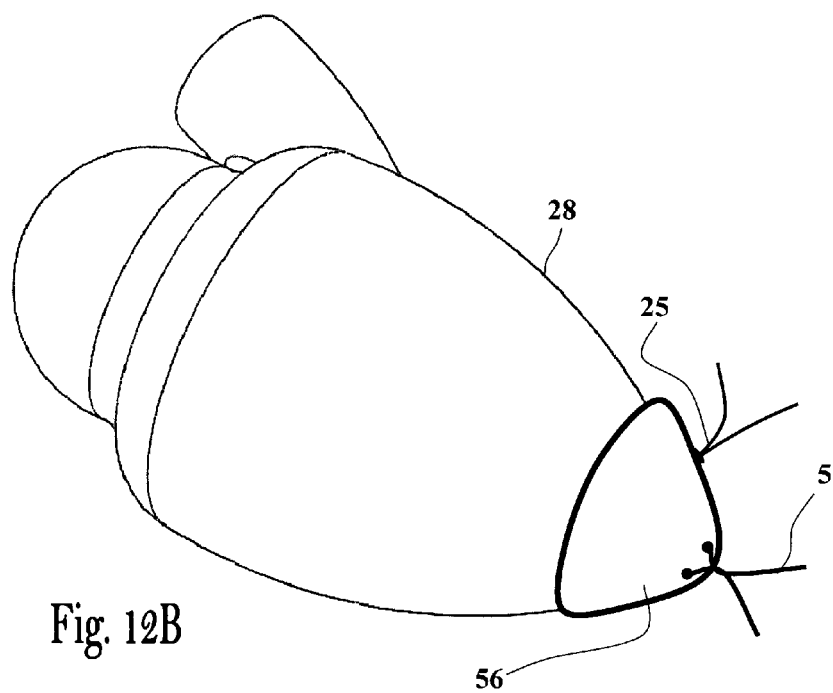

As demonstrated in FIGS. 12A and 12B, fixation suture string 5 may be attached to an external button 55, or to an apical cup 56, for providing a firm fixation and location of the ventricular function assisting device 10.

Figures 13A, 13B, 13C, 13D:
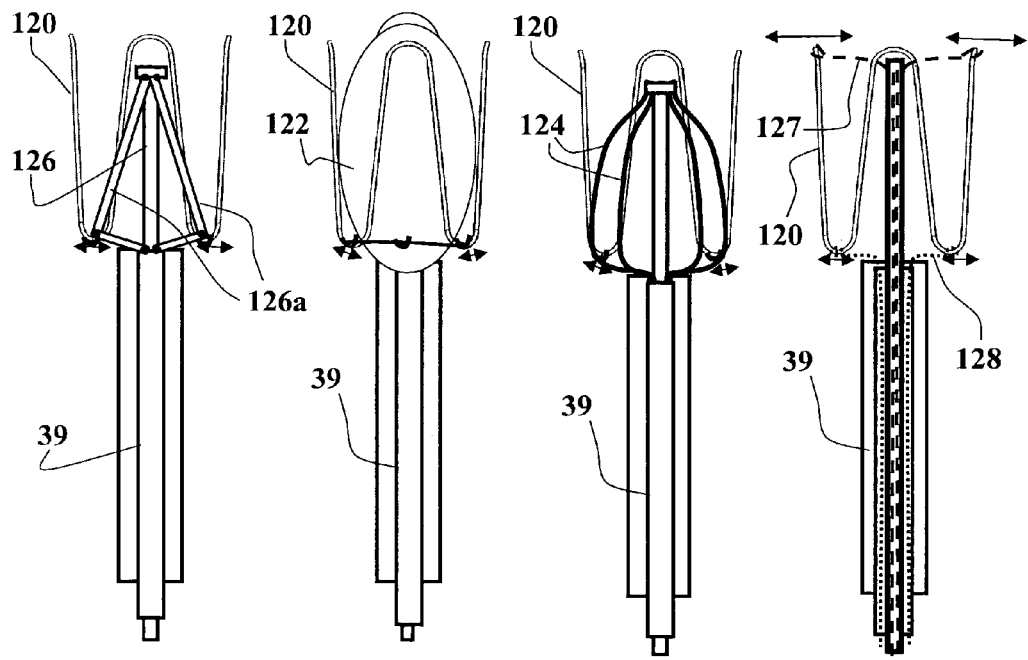

With reference to FIG. 13A to 13D, the ventricular function assisting device 10 can be opened into a deployed state by means of different deployment means, capable of gradually opening its arms in the radial direction, from the bottom to the top of the device or from the top to the bottom of the device. With reference to FIG. 13A the ventricular function assisting device of the invention 120 may be deployed into the heart 28 by means of a delivery tool comprising an umbrella-like mechanism 126 comprising movable arms 126a attached at the end of inner tube which are adapted to open device 120 against the heart tissue. FIG. 13B demonstrates another possible opening mechanism, wherein balloon 122 attached at the end of inner tube 39 is utilized for opening the device 120, by filling it with an inflation media. In another alternative implementation, demonstrated in FIG. 13C, wires 124, attached to the lower part of device 120, such that a basket like-shape is formed, are utilized for deploying device 120 in heart 28. In another alternative implementation, demonstrated in FIG. 13D, two sets of wires, 127 and 128, are used for deploying device 120, wherein one set of wires 127 is attached to the upper part of the arms of device 120, and the second set of wires 128 is attached to the lower part of the arms of device 120.

The present invention is also directed to ventricular function assisting devices suitable for implantation by means of a delivery tube, and to catheter apparatuses and methods for carrying such catheterization implantations. In these embodiments of the ventricular function assisting device of the invention two or more "arms" are connected at one end thereof to a base element adapted to be attached to the apex inside the left ventricle by means of anchoring means, wherein the free ends of the arms and/or portions thereof are disposed over inner wall sections of the ventricle. At least some portion(s) of the arms of the ventricular function assisting device are made elastic such that it capable of storing energy originated from the heart motion, taken from the myocardium movement during the systole, and releases the energy stored in it during the diastole, thereby augmenting diastolic performance of the heart. The device may be implanted in a ventricle in a preloaded state (i.e., the diameter of the device outside of the heart ventricle in a top view perspective when its arms are in a fully deployed state is greater than the diameter of the ventricle). In this way, additional elastic potential energy is stored in the bent arms of the device during the systole, as the arms are further pressed radially inwardly by the wall of the heart toward each other, whereas in diastole, as the ventricle walls are expanded and the arms of the device move radially outward, the elastic potential energy stored therein is released, while said preload ensures that the device is continuously loaded with elastic potential energy until the end of the diastolic phase, thereby available for diastolic performance augmentation.

Figures 14A, 14B:
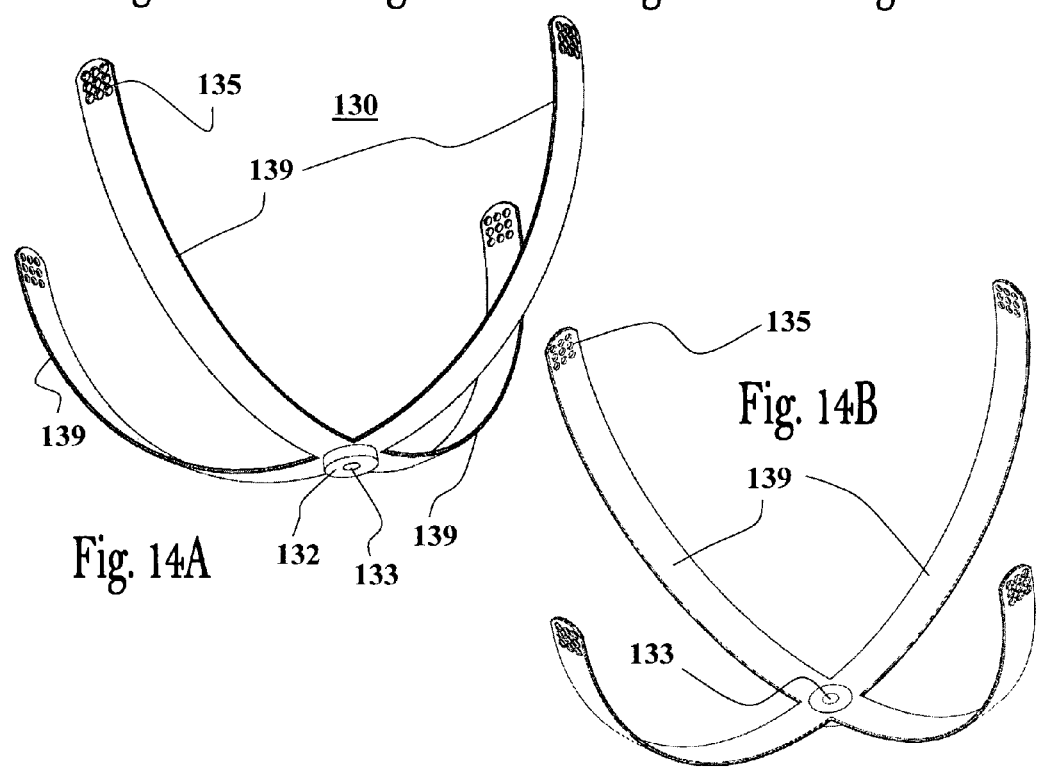
FIGS. 14A and 14B respectively show bottom and top perspective views of four-arms ventricular function assisting device of the invention which arms are made from tube by laser cut.

FIGS. 14A and 14B show perspective views of four-arms ventricular function assisting device 130 of the invention designed for implantation by a catheterization or trans apical procedures. In this preferred embodiment 130 the arms 139 are attached perpendicularly relative to each other to a base section 132, thus forming a cross shape in top or bottom view (not shown). The base section 132 is preferably made from a relatively thin disk element comprising a pass through bore 133 for attaching device 130 to the apex inside the ventricle. The upper portion of the free end of arms 139 preferably comprises an array of holes 135 adapted for promoting tissue ingrowth. Arms 139 are preferably elastic curved arms having a outward curvature corresponding to heart ventricle shape, said elastic arms are preferably manufactured from biocompatible materials having elastic properties by a laser cutting or metalworking process, preferably by laser cutting. The length Of arms 139 may generally be in the range of 30 to 60 mm, preferably about 45 mm, and their thickness may generally be in the range of 0.1 to 1 mm, preferably about 0.3 mm. The diameter of holes 135 may be about 0.1 to 0.5 mm. The diameter of base section 132 may be of about 1 to 5 mm, and the diameter of pass through bore 133 of about 1 to 5 mm. Of course, these sizes may be changed according to specific dimensions of a treated heart.

FIGS. 15A and 15B respectively show top and perspective views of a three-arms ventricular function assisting device 140 of the invention designed for implant by a catheterization or trans apical procedures, which arms 149 are made in a stent-like configuration. Arms 149 are preferably, but not necessarily, attached to base section 142 in a typical three-arm star conformation, forming 120° angles between them. Base section 142 comprises a pass through bore 143 for allowing attaching it to the apex inside the ventricle by means of suitable anchoring means. Arms 149 may be manufacture by laser cutting from, but not limited to, Stainless steel, biocompatible metal alloy, nitinol, or conichrome alloy, forming mesh structure having rhombus, or other suitable geometry, shaped apertures (e.g., 3× stent geometry), thereby producing elastic arms capable of being elastically bent along their lengths. This mesh configuration of the arms promotes tissue ingrowth and allows the arms to elastically bend inwardly in radial direction responsive to systolic heart retractions, and in sideway directions along their lengths responsive to heart twist movements. The length of arms 149 may generally be in the range of 30 to 60 mm, preferably about 45 mm, and their thickness may generally be in the range of 0.1 to 0.5 mm, preferably about 0.3 mm.

Figure 16B:
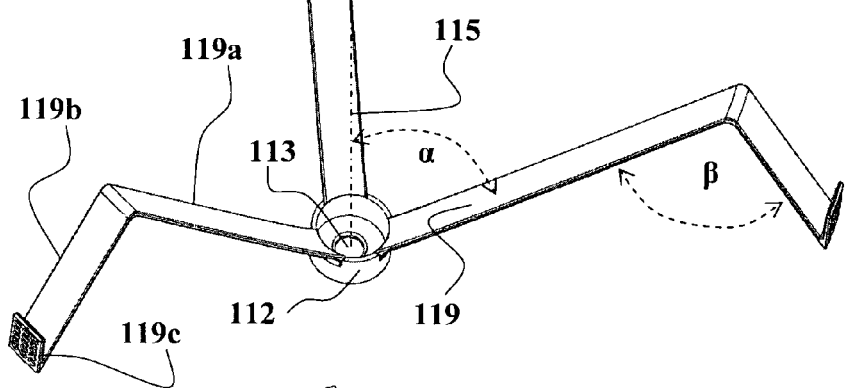

FIGS. 16A to 16F show perspective views of ventricular function assisting devices of the invention designed for implant by a catheterization or trans apical procedures, which arms comprise elastic slanted sections. Device 150 in FIG. 16A is a three-arms device comprising elastic arms 159 attached to a base section 152, preferably but not necessarily, in a typical three-arms conformation, wherein the upper portions 159*b* of elastic arms 159 is bent outwardly and their tip sections are bent upwardly perpendicular to upper portions 159*b* in order to define an attachment surface 159*c* with the heart tissue. Tip sections 159*c* of elastic arms 159 preferably comprise an array of apertures 159*p* adapted for promoting tissue ingrowth. Lower sections 159*a* of elastic arms 159 are preferably slanted relative to the longitudinal axis 155 of device 159 forming an acute angle α of about 20 to 80 degrees therebetween. The upper sections 159*b* of elastic arms 159 is preferably bent to put upper portions 159*b* more or less parallel to base section 152. Base section 152 is preferably made in form of a cup comprising a central hole 153 in its base for allowing attachment thereof to the apex inside the heart ventricle by means of suitable anchoring means. This configuration allows elastic movements of upper section 159*b* relative to lower section 159*a* in response to systolic and diastolic heart movements.

FIG. 16B shows a similar three-arms device 110 wherein the upper portions 119*b* of elastic arms 119 are bent such that an acute angle is established between its lower section 119*a* and its upper section 119*b*. This configuration provides improved elasticity between the lower sections 119*a* and the upper sections 119*b* of elastic arms 119. Elastic arms 119 are attached to base section 112 in a typical three-arms star conformation, said base section 112 is made in form of a cup comprising a central hole 113 in its base for allowing attachment thereof to the apex inside the heart ventricle by means of suitable anchoring means. The tip sections 119*c* of elastic arms 119 are bent upwardly to define an acute angle between them and upper sections 159*b* in order to define an attachment surface with the heart tissue. Tip sections 119*c* of elastic arms 119 preferably comprise an array of apertures 119*p* adapted for promoting tissue ingrowth. Lower sections 119*a* of elastic arms 119 are preferably slanted relative to the longitudinal axis 115 of device 110 forming an acute angle α of about 20 to 80 degrees therebetween. The upper sections 119*b* of elastic arms 119 is preferably bent in a downward direction thus forming an angle β of about 20 to 120 degrees between the upper section 119*b* and the lower sections 119*a* of elastic arms 119. Similarly, this configuration allows elastic movements of upper section 119*b* relative to lower section 119*a* in response to systolic and diastolic heart movements.

Devices 150 and 110 are preferably manufactured from biocompatible materials having elastic properties by a laser cutting or metalworking process, preferably but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The lengths of arms 159 and 119 may generally be in the range of 30 to 60 mm, preferably about 40 mm, and their thickness may generally be in the range of 0.1 to 0.5 mm, preferably about 0.3 mm. The diameter of holes 159*p* and 119*p* provided in tip section 159*c* and 119*c* may be of about 0.1 to 0.5 mm. The diameter of cup shaped base sections 152 and 112 may be of about 1 to 5 mm, and the diameter of their central holes 153 and 113 is preferably about 1 to 5 mm.

Figure 16C:
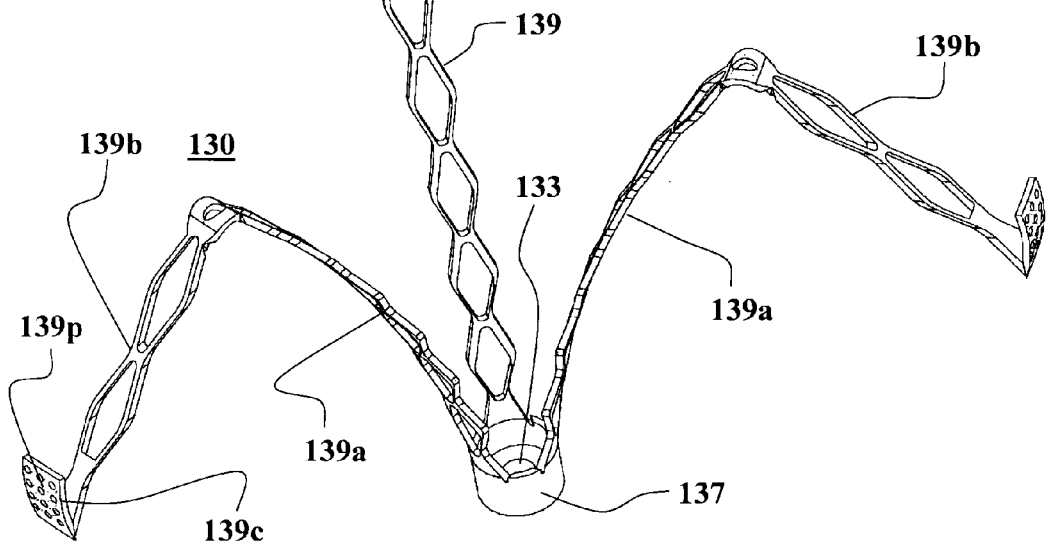

FIG. 16C shows another embodiment 130 of the ventricle function assisting device 110 shown in FIG. 16B, wherein the arms 139 of device 130 are made by laser cutting in a stent-like configuration forming a sequence of serially connected rhombus shaped sections. Of course other geometrically shaped sections may be produced by the laser cutting in the manufacture process of arms 139. Arms 139 are attached to a cup-shape base section 132, preferably not necessarily in a typical three-arms star conformation, wherein the cup-shaped section 132 comprises a central hole 133 in its base for allowing it to be attached to the apex inside the heart ventricle by means of suitable anchoring means. In a similar fashion, upper section 139*b* of arms 139 is bent to form an acute angle relative to lower section 139*a*. The tip sections 139*c* of arms 139 are preferably flat rectangular sections forming an acute angle relative to upper sections 139*b*, wherein each of the tip sections 139*c* comprises an array of apertures 139*p* adapted to promote tissue ingrowth. This configuration of ventricular function assisting device 130 allows the arms to elastically bend in a radial direction inwardly in response to systolic heart movements, and in sideway directions in response to heart twist movements.

FIG. 16D show a three-arms device 135 similar to device 130 shown in FIG. 16C, which arms are manufactured in a stent-like configuration forming a mesh of rhombus shaped holes. Of course, other geometrical shapes of the holes may be alternatively used. Similarly, arms 136 of device 130 are attached to a cup-shaped base section 134, preferably but not necessarily in a typical three-arms conformation. The upper sections 136*b* of arms 136 are bent to form an acute angle relative to their lower sections 136*a*, and the tip sections 136*c* are bent to define attachment surface with heart tissue thereby forming an acute angle relative to upper sections 136*b*. The tip sections 136*c* are preferably also made in a stent-like configuration having rhombus shaped holes to promote tissue ingrowth.

Devices 130 and 135 are preferably manufactured from elastic biocompatible materials suitable for laser cutting, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The lengths of arms 139 and 136 may generally be in the range of 30 to 60 mm, preferably about 40 mm, and their thickness may generally be in the range of 0.1 to 0.52 mm, preferably about 0.3 mm. The diameter of holes 139p provided in tip section 139c may be of about 0.1 to 0.5 mm. The diameter of cup shaped base sections 137 and 134 may be of about 1 to 5 mm, and the diameter of their central holes 133 and 137 is preferably about 1 to 5 mm.

FIG. 16E shows an embodiment of a four-arms device 115 of the invention comprising elastic arms 116 attached to a cup-shaped base section 114 such that straight angles are obtained between adjacent arms, thereby forming a cross shape in top or bottom view (not shown). Lower sections 116a of elastic arms 116 are preferably slanted relative to the longitudinal axis 117 of device 115 thus forming an acute angle α of about 20 to 80 degrees therebetween. The upper sections 116b of elastic arms 116 is preferably bent in a downward direction thus forming an angle β of about 20 to 120 degrees between upper sections 116b and the lower sections 116a of elastic arms 116. Similarly, this configuration allows elastic movements of upper section 116b relative to lower section 116a in response to systolic and diastolic heart movements. Elastic arms 116 further comprise tip sections 116c defining attachment surfaces with heart tissue, said tip sections 116c are bent upwardly such that acute angles are formed relative to upper sections 116b. An array of apertures 116p is preferably provided in tip sections 116c in order to promote tissue ingrowth.

FIG. 16F shows a preferred embodiment of a six-arms ventricular function assisting device 161 of the invention. Device 161 comprises a set of three long elastic arms 165 and another set of three short elastic arms 167, said arms are attached to a cup-shaped base section 162 having a central attachment hole 164 in its base and they are arranged such that between two neighboring arms from the set of long arms 165 there is disposed one arm from the set of short arms 167. Long arms 165 comprise lower, upper and tip, sections, as in arms 119 and 116, which sections are bent in a similar fashion to form acute angles therebetween, and which tip section also comprise an array of apertures for promoting tissue ingrowth. Short arms 167 are preferably bent relative to the longitudinal axis (not shown) of device 161 forming an acute angle relative to it, said acute angle is more less the same as the angle formed between the lower sections of long arms 165 and said longitudinal axis. Short arms 167 further comprise tip sections at their free end, said tip sections are bent downwardly to define attachment surfaces with the heart tissue, said attachment surfaces are more or less parallel to the longitudinal axis of the device. Device 161 may be manufactured from similar materials and using similar manufacture techniques, as of devices 110 and 115. The lengths of long arms 165 may generally be in the range of 30 to 60 mm, preferably about 40 mm, the lengths of short arms 167 may generally be in the range of 10 to 30 mm, preferably about 20 mm, and the thicknesses of both sets of arms may generally be in the range of 0.1 to 0.5 mm, preferably about 0.3 mm.

FIGS. 17A to 17C show perspective views of ventricular function assisting devices of the invention having elastic arms arranged on a central post and which are designed for implant by a catheterization or trans apical procedures. FIGS. 17A and 17B show a three-arms device 160 having elastic arms 169 having a long section 169a attached to the upper end of post 160p. Long sections 169a of arms 169 are slanted downwardly relative to post 160p, such that acute angles α are formed therebetween. Arms 169 further comprise a short section 169b which is slanted upwardly to define an attachment surface with the heart tissue, thereby forming an acute angle β relative to the long sections 169a of arms 169. The attachment surfaces of short sections 169b preferably have a curved shape for improved contact with the heart tissue. Post 160p comprises a central pass through bore 160a for attaching it to the apex inside heart ventricle by means of screws or barbs, for example.

FIG. 17C shows another embodiment of a three-arms device 163 which elastic arms 166 are arranged on a central post 163p, wherein each of said arms 166 comprises a first section 166a attached to post 163p, said first section 166a is bent downwardly such that an acute angle α of about 20 to 80 degrees is obtained relative to post 163p. Arms 166 further comprise upwardly slanted intermediate sections 166b forming angles β of about 50 to 150 degrees relative to first sections 166a, and downwardly slanted tip sections 166c forming angles γ of about 20 to 120 degrees relative to intermediate section 166b, thereby defining attachment surfaces with the heart tissue. Attachment surfaces 166c may comprise anchoring pins 166q adapted to achieve a grip to the heart tissue. The lengths of arms 166 may generally be in the range of 20 to 60 mm, preferably about 35 mm, and their thickness may generally be in the range of 0.1 to 0.52 mm, preferably about 0.3 mm.

FIGS. 18A to 18E illustrate embodiment of the ventricular function assisting devices of the invention using springs elements in the devices' arms. FIGS. 18A and 18B respectively show a top view and a perspective view of a three-arms device 20 which arms 21 are attached by means of springs 23s to a base section 23 comprising a pass through bore 23b configured to attached device 20 to the apex inside the heart ventricle. Arms 21 are preferably curved about their longitudinal axis to define a curved attachment surface 21f with the heart tissue. Arms 21 may comprise a base portion 21a at their lower ends to which spring elements 23s are attached, and an outwardly curved portion 21b adapted to contact the heart tissue. Spring elements 23s are preferably a type of torsion springs comprising one or more torsion loops configured as an elastic hinge for connecting between base portions 21a of arms 21 and base section 23 and for allowing radial movement of arms 21 thereabout. Arms 21 may be manufactured from rigid biocompatible materials, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The lengths of arms 21 may generally be in the range of 20 to 60 mm, preferably about 45 mm. Spring elements may be manufactured form any suitable elastic biocompatible material, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol.

FIG. 18C shows a perspective view of an elastic arm 29 comprising spring elements 29a 29b 29c distributed along its length, where said spring elements 29a 29b 29c are preferably made in a form of torsion springs comprising one or more torsion loops. Elastic arms 29 is preferably made from a turned wire made from an elastic biocompatible material, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The length of elastic arm 29 may be the same as of arms 21 shown in FIGS. 18A and 18B, and few such elastic arms may be similarly connected to a base section 23 by means of connecting pin 29f formed at its lower end and thereby construct a ventricular function assisting device which arms 29 are capable of being bent radially and in sideway directions in response to ventricular heart movements.

FIG. 18D shows an embodiment 26 of the elastic arm 29 shown in FIG. 18C comprising interfacing members 26a 26b 26c. Interfacing member 26a is attached between spring elements 29a and 29b, and interfacing member 26b is attached between spring elements 29b and 29c, where interfacing member 26c is attached to the longer section of elastic arm 29 extending from spring element 29c to the upper tip of the elastic arm. Interfacing members 26a 26b 26c may comprise a central groove configured to receive and hold the respective portions of elastic arm 29 attached to these interfacing members. Interfacing members may be manufactured from an elastic biocompatible material, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol.

FIG. 18E shows a perspective view of a double wire embodiment 77 of elastic arm 29 shown in FIG. 18D. In this embodiment elastic arm 77 is made from a turned elastic wire such that a pair of parallel arms 29', each similar in shape and structure to arm 29 shown in FIG. 18C, are obtained. Accordingly, elastic arm 77 comprises pairs of adjacent spring elements 29a' 29b' 29c', and a pair of connecting pin 29f which may be used to connect a number of elastic arms 77 to a base section and thereby construct a ventricular function assisting device which arms 77 are capable of being bent radially and in sideway directions in response to ventricular heart movements.

FIGS. 19A and 19B respectively show a perspective view and a top view of three-arms embodiment 24 of the ventricular function assisting device of the invention having elastic arms 24a and a spiral-star base section 24s. Ventricular function assisting device 24 may be attached to the apex inside the heart ventricle by means suitable anchoring means attached to a bore 24c formed at the point of connection of elastic arms 24a in the spiral star base section 24s. As seen in FIGS. 19A and 19B the upper portions of arms 24a is relatively straight and having a slight outward curve to better interface it with the internal shape of the heart ventricle, while their lower portions spirally curved downwardly to form an inverted spiral star dome shape of base section 24s. This configuration of device 24 allows its arms 24a to be bent both in radial and sideway directions as it responses to ventricle heart movements. Device 24 may be manufactured by laser cutting technique, from elastic biocompatible materials, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The lengths of the relatively straight portion of arms 24a may generally be in the range of 20 to 60, preferably about 45 mm, and the diameter of inverted spiral star dome of base section 24s may generally be in the range of 20 to 60 mm, preferably about 35 mm.

Figure 20B:
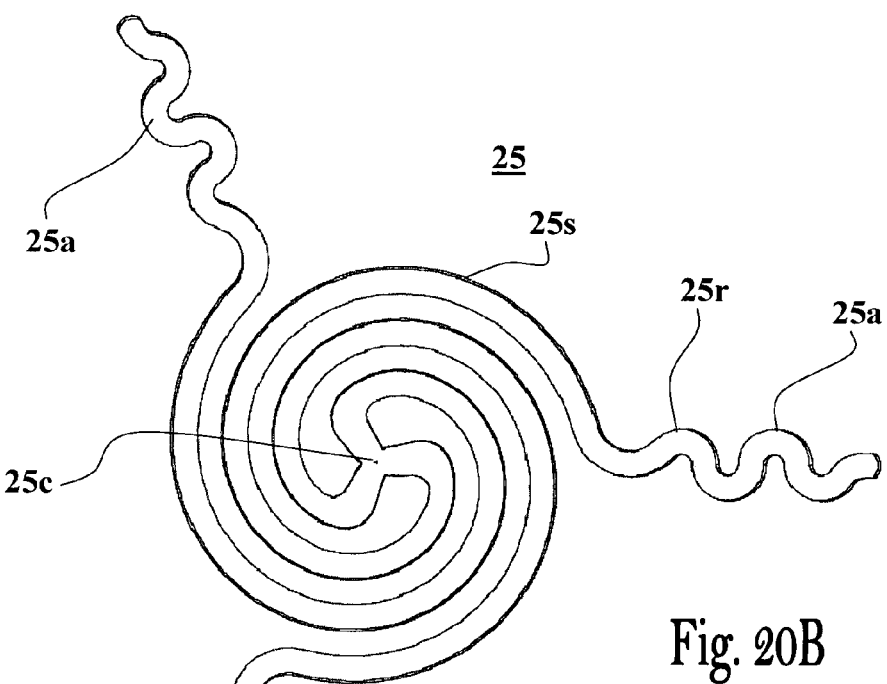

FIGS. 20A and 20B respectively show a perspective view and a top view of three-arms embodiment 25 of the ventricular function assisting device 24 shown in FIGS. 19A and 19B, wherein the upper portions 25r of the arms 25a of device 25 comprise elastic corrugations and their lower portions 25s are spirally curved downwardly to form an inverted spiral star dome shape. In this embodiment, which is substantially similar to device 24 shown in FIG. 19, the flexibility of the upper portions of arms 25a is improved by means of the corrugated configuration which allows it to be bent in sideway and longitudinal directions along its length.

Figure 21A:
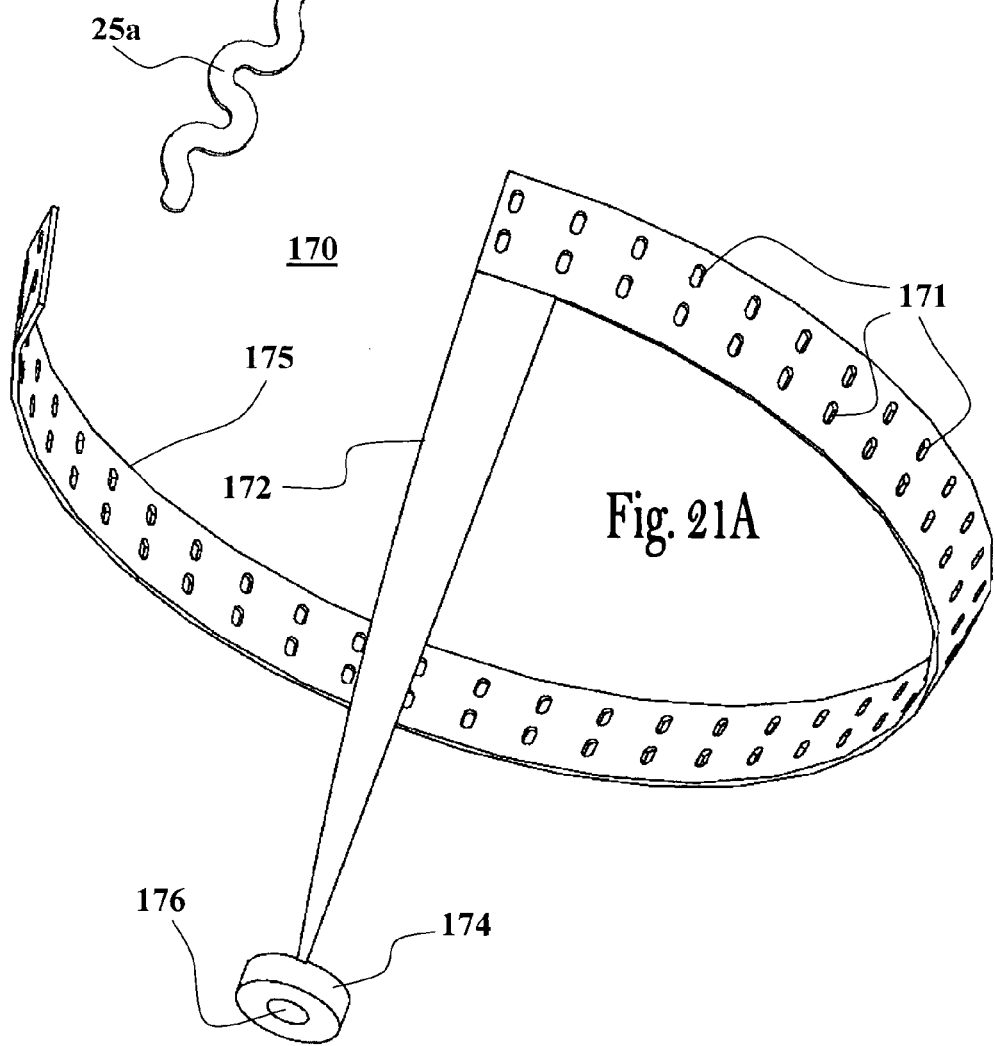

FIGS. 21A and 21B show perspective views of ventricular function assisting devices of the invention designed for implantation by a catheterization or trans apical procedures, and which comprise elastic circular attachment sections. Device 170 shown in FIG. 21A comprise an elastic circular attachment section 175 attached by means of a connecting strip 172 to a base section 174 comprising a pass through attachment bore 176. Elastic circular attachment section 175 is adapted to be mounted inside the heart ventricle such that its outer surface is pressed against the heart tissue. Elastic circular attachment section 175 preferably comprises a plurality of apertures 171 distributed over its surface for promoting tissue ingrowth and adhesion. Elastic circular attachment section 175 is preferably designed to span over a circular sector of about 90 to 350 degrees, its width may generally be in the range of 1 to 20 mm, its thickness in the range of 1 to 4 mm, and the diameter of circular attachment section 175 may generally be in the range of 50 to 100 mm.

The device 178 shown FIG. 21B comprises an upper circular attachment section 175a and a lower circular attachment section 175b, both attached by means of a connecting strip 172 to a base section 174 comprising a pass through attachment bore 176. The geometrical dimensions of circular attachment sections 175a and 175b are substantially similar to those of circular attachment section 175 of device 170 shown FIG. 21A, where the diameter of lower circular attachment section 175b are generally be in the range of 15 to 50 mm.

Ventricular function assisting devices 170 and 178 may be manufactured by laser cutting or metalworking, from suitable elastic biocompatible materials, such as but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. In addition, the various ventricular function assisting devices described hereinabove may further be covered by a layer of material suitable for promoting tissue growth and/or with hemocompatible coating and/or drug delivery agents, such as, but not limited to, Dacron, Teflon, ePTFE, or any other biocompatible polymeric material suitable for these purposes.

Figure 22C:
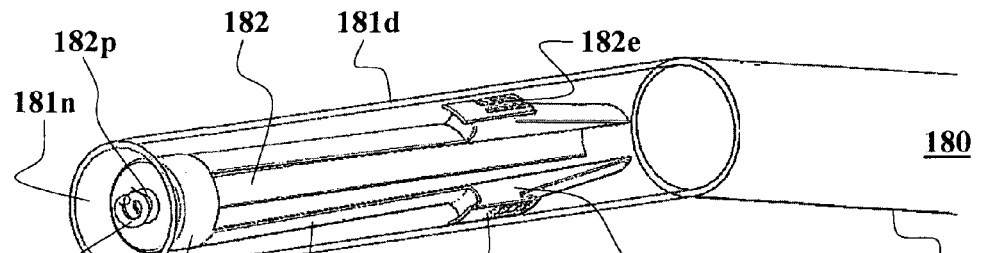

FIGS. 22A to 22E illustrate a delivery tube 180 suitable for implanting the ventricular function assisting devices shown in FIGS. 14 to 18 in a catheterization procedure. In FIGS. 22A and 22B the delivery tube 180 comprises an elongated flexible tube 181 comprising a three-arms ventricular function assisting device 182 of the invention placed in its distal end section 181d in a folded state. In this state the elastic arms 182a of device 182 are pressed in a radial inward direction toward each other in order to reduce the device diameter to allow it to be inserted into the distal end section 181d of tube 181 via distal opening 181n. Ventricular function assisting device 182 also comprise tip sections 182q having attachment surfaces 182d on which anchoring pins 182e may be formed.

Figure 22D:
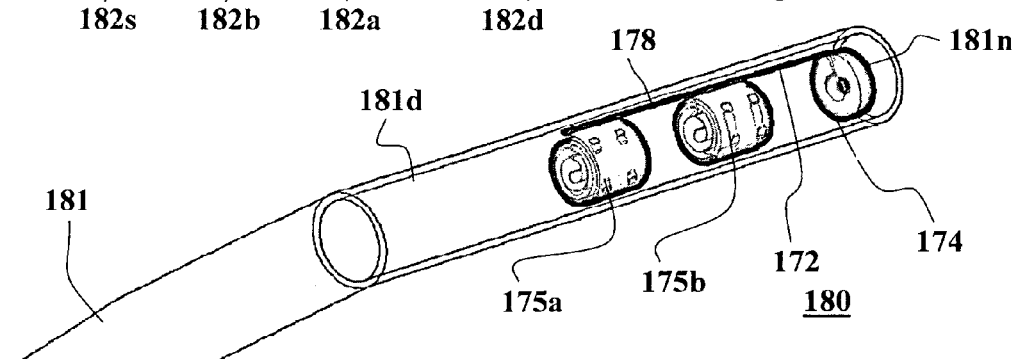
Figure 22E:
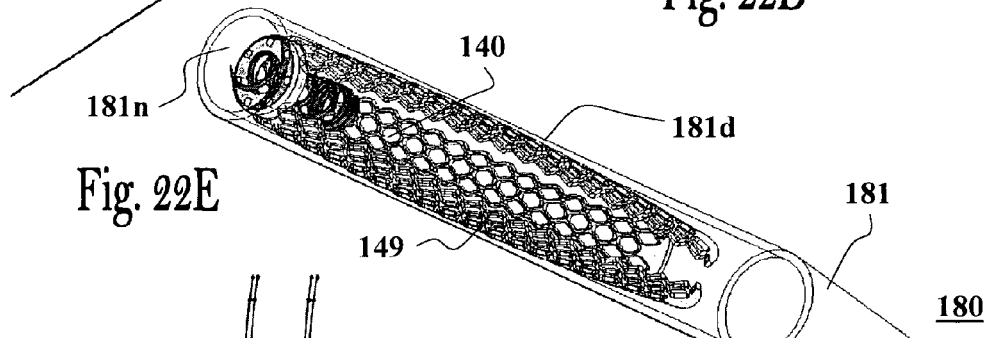

FIG. 22C shows ventricular function assisting device 182 placed inside distal end section 181d of tube 181 with an anchoring helical element 182s disposed in the attachment bore 182p of its base section 182b. FIG. 22D shows delivery tube 180 with ventricular function assisting device 178 (shown FIG. 21B) placed inside distal end section 181d of tube 181, wherein the circular attachment sections 175a and 175b are tightly rolled to accommodate device 178 inside distal end section 181d of tube 181. FIG. 22E shows delivery tube 180 with ventricular function assisting device 140 (shown FIGS. 15A and 15B) placed inside distal end section 181*d* of tube 181 in a folded state wherein its elastic arms 149 are radially pressed toward each other in order allow fitting inside distal end section 181*d* of tube 181.

Figure 23A:
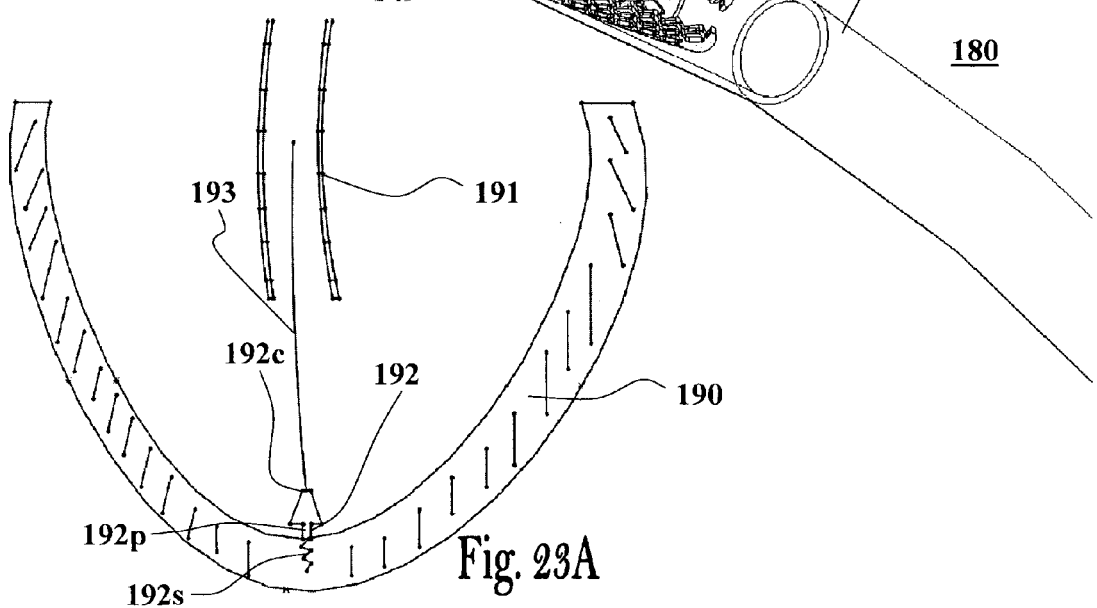

FIGS. 23A to 23E schematically illustrate a possible catheterization implantation procedure suitable for implanting the ventricular function assisting devices shown in FIGS. 14 to 18 for treating DHF. FIG. 23A schematically illustrates introduction of a delivery system into the left ventricle 190, the delivery system comprises a guiding tube 191 and a torque wire 193 passing thereinside. The inner diameter of the delivery system is preferably not greater than 12 Fr. The distal end of torque wire 193 comprises an anchoring element 192 attached to it by means of a connecting mechanism, said connecting mechanism may be implemented by means of screwing, clicking, or a push-pull mechanism. Anchoring element 192 comprises a helical (or spiral) section 192*s* capable of being screwed into the heart tissue. As shown in FIG. 23A, once helical section 192*s* is screwed into the tissue at the apex inside the ventricle 190 delivery tube 191 is retracted proximally and removed from the vascular system of the treated subject.

FIG. 23B schematically illustrates insertion of the delivery tube 180 into ventricle 190 over torque wire 193 with ventricular function assisting device 182 of the invention placed inside distal end portion 180*d* of delivery tube 180.

In FIG. 23C the delivery tube reaches anchoring element 192 and the attachment bore provided in the base section of device 182 engages a retaining post 192*p* of anchoring element 192, said retaining post 192*p* comprises conical shape stopper 192*c* configured to receive base section of device 182 and prevent it from being released from the grip obtained by anchoring element 192. FIG. 23C schematically illustrates removal of delivery tube 180 by retracting it proximally, which as shown in FIG. 23D, results in the discharge of ventricular function assisting device 182 and deployment of its elastic arms on the inner walls of ventricle 190. In steps shown in FIGS. 23C and 23D the orientation of device 182 is adjusted according to the internal anatomy of the ventricle by manipulating delivery tube 180. Finally in FIG. 23E delivery catheter 191 (not shown) is inserted into ventricle 190 with a securing element 199 which is attached to stopper 192*c* by an attachment mechanism for preventing device 182 from being released from anchoring element 192. Thereafter, the torque wire 193 is released and removed.

FIGS. 23F and 23G respectively illustrate a side sectional view and a perspective view of the torque wire 191 and anchoring element in an engaged and detached states. As exemplified in these figures anchoring element 192 may be configured in a form of a cylindrical body comprising a distal flange 192*f* forming a neck section 192*n* on which helical anchoring screw 192*s* is attached. The proximal side of anchoring element is made hollow to form a socket 192*b* and a waist section 192*w* between said socket 192*b* and said flange 192*f*, said waist section 192*w* is designed to be received in the attachment bore 182*p* of ventricular function assisting device 182. The distal end of torque wire 191 comprises a releasable attachment spring lock mechanism 191*h* adapted to fit into socket 192*b* and attach thereinto by means of press springs 191*k*. Press springs 191*k* are configured to fit into vertical slots 192*t* provided in opposite sides of socket 192*b*. The connection obtained between releasable attachment spring lock mechanism 191*h* and anchoring element 192 may be released by introducing an additional tube (not shown) which is adapted for pressing internally press springs outside of vertical slots 192*t* and thereby release the attachment between these components.

FIGS. 24A and 24B schematically illustrate a delivery tube 201 suitable for implanting the ventricular function assisting devices of the invention by a single step catheterization procedure. The delivery tube 201 preferably comprises a proximal handle (not shown) adapted for steering, turning, pushing and pulling delivery tube 201, and its inner diameter is preferably about 16-18 Fr. The distal section 201*d* of delivery tube 201 is preferably made flexible and it is configured to receive a ventricular function assisting device 182 of the invention in a folded state (i.e., wherein the elastic arms of the device are pressed toward each other). Torque wire 202 passing along the length of delivery tube 201 is made in a form of a hollow tube in which guide wire 205 is passed. In this embodiment an anchoring element 203 having an internal passage is attached to the distal end of torque wire 202, such that guide wire 205 also passes through the internal passage of anchoring element 203. Ventricular function assisting device 182 is fitted over a waist section provided in anchoring element 203, and a helical or spiral anchor 203*s* is provided attached to anchoring element for allowing it to be screwed into the heart tissue.

The delivery tube preferably comprises a proximal handle (not shown) adapted for steering, turning, pushing and pulling delivery tube 201, and its inner diameter is preferably about 16-18 Fr.

In this implantation procedure the delivery tube 201 comprising torque tube 202, anchoring element 203, and ventricular function assisting device 182, is advanced via the vascular system over guide wire 205 into the treated heart ventricle. Inside the heart ventricle the helical or spiral anchor 203*s* is advanced outside of delivery tube 201 via it tapered end by pushing torque tube 202 distally. Thereafter, helical or spiral anchor 203*s* is screwed into the heart tissue by turning of the torque wire 202 via its handle (not shown). Then, the ventricular function assisting device 182 is gradually discharged by retracting delivery tube proximally, and the orientation of device 182 is adjusted according to the internal anatomy of the ventricle by manipulating delivery tube 201. Once the needed orientation is obtained, the entire length of device 182 is discharged from delivery tube 201 such that its flexible arms change into a deployed preloaded conformation as they are pressed against the internal walls of the ventricle. Finally, the delivery tube 201 is retracted distally, the attachment of torque tube 202 to anchoring element 203 is released, and torque tube 202 and guide wire 205 are retracted proximally outside of the vascular system.

FIGS. 25A to 25F schematically illustrate various anchoring elements suitable for attaching the ventricular function assisting devices in catheterization approach shown in FIGS. 14 to 18 to a ventricular apex. FIG. 25A schematically illustrates an anchoring element 210 comprising a helical/spiral anchor 210*s* configured to be screwed into the tissue of ventricle 190, and screw head 210*t* attached to helical/spiral anchor 210*s*. Helical/spiral anchor 210*s* may be implemented by a simple spring, preferably made from a radiopaque material, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The diameter of Helical/spiral anchor 210*s* may generally be in the range of 1 to 5 mm, and the diameter of the wire from which it is made may be between 0.2 to 0.5 mm. The length of Helical/spiral anchor 210*s* is adapted such that it will not pass the entire width of the ventricle tissue, for example in range of 4 to 20 mm.

FIG. 25B illustrates an anchoring element 211 comprising fixating barb elements 211*b*. In this implementation anchoring element 211 is passed through the width of the ventricle wall and it is fixated in this state by means of barb element 211*b* attached at each of its ends. Each of the barb elements 211*b* preferably comprises 3 to 6 barbs. Anchoring element 211 and its bar elements 211*b* are preferably made from a radiopaque material, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The diameter of anchoring element 211 may generally be in the range of 0.5 to 1.5 mm, and its length between 4 to 20 mm.

FIGS. 25C to 25F illustrate a procedure of implanting an anchoring element 215 of the invention comprising several hooks 215*v*, which is introduced into the myocardium 190 by means of a needle 214. In this procedure needle 214 with anchoring element 215 comprised in its distal end is introduced into the apex tissue, and the anchoring element 215 is then discharged into the tissue by pulling needle 214 out of the tissue. Anchoring element 215 is preferably made from a radiopaque material, such as, but not limited to stainless steel alloys, super alloys (35N LT, MP35N, L605 etc.), preferably from FWM1058 alloy (also known as Conichrome™—a cobalt-chromium-nickel-molybdenum-iron alloy specified by ASTM F1058 and ISO 5832-7) or Nitinol. The diameter of anchoring element 215 may generally be in the range of 0.5 to 3 mm, and its length between 3 to 20 mm, depending on the width of apex wall.

FIGS. 26A and 26B show a simulation of an implantation procedure following the catheterization approach of the invention by means of the delivery tube 180 shown in FIG. 16B. FIG. 26A shows the step of attaching the ventricular function assisting device 110 (shown in FIG. 16B) comprised inside the delivery tube 180 in a folded state. FIG. 26B shows removal of the delivery tube 180, and FIG. 26C shows deployment of the ventricular function assisting device 110 inside the heart ventricle 190.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different tubes, shafts, and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A ventricular function assisting device comprising two or more arms each of which comprising a bottom end, a free top end and an intermediate section extending between said ends, wherein each arm is substantially a planar arm, wherein said bottom ends of said two or more arms are attached in a base section of said device thereby forming a flower cup configuration, and wherein said two or more arms comprise elastic elements or portions configured such that they are capable of elastically bending in radial directions relative to longitudinal axis of said flower cup configuration, and wherein said device is capable of being set into two conformations: i) a folded conformation, in which said two or more arms are pressed inwardly in a radial direction towards each other thus allowing fitting said ventricular function assisting device in a delivery tube or sheath in said folded conformation; and ii) a deployed conformation, in which said two or more arms are opened in a radial outward direction, wherein said device is adapted to be attached at said device base section to an apex inside a heart ventricle in said deployed conformation such that at least said arms' free top ends are pressed against the walls of said heart ventricle thereby allowing said two or more arms to elastically bent in radial direction during contractions of said heart ventricle and thereby store potential energy in said elastic elements or portions provided therein, and to release said energy during expansions of said heart ventricle.

2. A ventricular function assisting device according to claim 1, wherein the two or more arms are further adapted to elastically bend in sideway directions in response to twist movements and longitudinal movements of the heart ventricle in which said ventricular function assisting device is implanted.

3. A ventricular function assisting device according to claim 1, wherein the base section of said ventricular function assisting device comprises a disk element, said disk element comprising a central pass through bore adapted for attaching said disk element to the apex inside the heart ventricle and a circumferential surface to which the bases of the one or more arms are attached.

4. A ventricular function assisting device according to claim 1, wherein the base sections of said ventricular function assisting device comprises elastic torsion loops elements configured to elastically connect the bottom ends of adjacent arms of said ventricular function assisting device, wherein said torsion loops are further employed to attach said ventricular function assisting device to the apex inside the heart ventricle by means of suture strings passing through and/or attached to said torsion loops elements.

5. A ventricular function assisting device according to claim 1, wherein the base section of said ventricular function assisting device comprises a cup shaped element with a base having an attachment bore provided in said cup shaped element base and a circumferential wall to which the arms of said ventricular function assisting device are attached.

6. A ventricular function assisting device according to claim 1, wherein portions of the arms, or the entire surface, of said ventricular function assisting device are covered by a padding element.

7. A ventricular function assisting device according to claim 6, wherein the padding element is adapted to promote tissue ingrowth.

8. A ventricular function assisting device according to claim 6, wherein the padding element is adapted to release a drug into the tissue of the heart.

9. A ventricular function assisting device according to claim 1, wherein the portions of the arms adapted to be pressed against the wall of the heart ventricle comprise apertures adapted to promote tissue ingrowth.

10. A ventricular function assisting device according to claim 1, wherein portions, or the entire area, of the arms, or the entire ventricular function assisting device, are covered by a layer of material suitable for promoting tissue growth.

11. A ventricular function assisting device according to claim 1, wherein the arms of said ventricular function assisting device are made from an elastic mesh having rhombus, or other geometry, shaped apertures.

12. A ventricular function assisting device according to claim 1, wherein the arms of said ventricular function assisting device further comprise elastic corrugations formed along their lengths, in their free top end, and/or in their bottom ends.

13. A ventricular function assisting device according to claim 1, wherein the arms of said ventricular function assisting device are attached to the base section by means of springs.

14. A ventricular function assisting device according to claim 1, wherein the arms of said ventricular function assisting device comprise one or more springs.

15. A ventricular function assisting device according to claim 1, wherein the bottom sections of the arms of said ventricular function assisting device are curved such that a spiral star structure is formed in the base section.

16. A ventricular function assisting device according to claim 1, wherein said device is made from an elastic wire or from a layered structure of elastic strips.

17. A method for implanting the ventricular function assisting device according to claim 1, the method comprising:
   opening a passage to the heart apex through the patient's chest;
   marking the papillary muscles for visualization by suitable marking means;
   performing a purse string at the heart apex for the insertion of a trans-apical sheath thereinto by means of a dilator;
   introducing delivery tool into the trans-apical sheath and advancing said delivery tool distally through the trans-apical sheath until the distal end of the delivery tube is introduced into the ventricle via the distal opening of the trans-apical tube, wherein said delivery tool comprises a delivery tube adapted to receive and hold the ventricular function assisting device in a folded state in said delivery tube distal end section and a hollow inner shaft slidably passing inside the delivery tube, said hollow inner shaft comprising a clamping mechanism adapted to releasably hold suturing string(s) attached to the base section of the ventricular function assisting device;
   advancing the ventricular function assisting device in a folded state through said delivery tube of said delivery tool into the heart by means of said inner hollow shaft;
   manipulating the orientation of the ventricular function assisting device relative to the papillary muscles markers for properly positioning said ventricular assisting device inside the heart ventricle;
   discharging the ventricular function assisting device inside the heart ventricle by distally pushing said inner hollow shaft, during which the ventricular function assisting device unfolds into a preloaded deployed state;
   retracting said delivery tool proximally;
   retracting said trans-apical sheath from the incision;
   fastening the purse string to close the incision; and
   suturing the incision by the purse string wires and the suturing string(s) to the apex tissue.

18. A method for implanting the ventricular function assisting device according to claim 1, the method comprising:
   making a small incision in an artery or vein, by means of a needle, or any other standard equipment generally used for performing catheterization procedures for accessing into a blood vessel;
   introduction through said incision a guiding tube comprising a torque wire slidably passing thereinside, wherein the torque wire comprises a distal end and wherein the distal end of the torque wire comprises an anchoring element releasably attached to said torque wire by means of a connecting mechanism;
   advancing said guiding tube with the torque wire comprised in said guiding tube through the vascular system into a heart ventricle;
   anchoring said anchoring element into an apex inside the ventricle;
   retracting said delivery tube proximally and removing said delivery tube from the vascular system of the patient;
   advancing a delivery tube flexible distal section into said ventricle over said torque wire until the delivery tube reaches the anchoring element, said delivery tube comprising said ventricular function assisting device placed inside a distal end portion thereof;
   attaching the base section of said ventricular function assisting device to said anchoring element;
   manipulating the orientation of said ventricular function assisting device to properly place said ventricular function assisting device thereinside;
   retracting proximally and removing said delivery tube thereby discharging said ventricular function assisting device such that the arms of the ventricular assisting device are pressed against the inner walls of ventricle in a preloaded state;
   releasing said torque wire from the anchoring element and removing said torque wire from the patient's body.

19. The method according to claim 18, further comprising inserting a delivery catheter comprising a securing element into the ventricle and attaching said securing element to the anchoring element.

20. A delivery system for implanting a ventricular function assisting device according to claim 1, comprising a delivery tube having a flexible distal section and comprising a tapering tip configured to receive said ventricular function assisting device in a folded state, a torque tube passing inside, and along the length of, said delivery teal tube, said torque tube is made in a form of a hollow tube, a guidewire slidably passing inside the torque tube, and an anchoring element releasably attached to said torque tube, wherein said anchoring element comprises a waist section adapted to receive the base section of said ventricular function assisting device, a distally attached helical or spiral anchor, and an internal passage provided along the length of said anchoring element.

21. A method for implanting a ventricular function assisting device by means of the delivery system of claim 20, comprising:
   making a small incision in an artery or vein as described hereinabove and introducing the guidewire through a vascular system into a heart ventricle;
   advancing the delivery tube comprising the torque tube, the anchoring element, and the ventricular function assisting device in the delivery tube flexible distal portion, via the vascular system over the guide wire into the treated heart ventricle;
   advancing the helical or spiral anchor outside of delivery tube via a tapered end tip of the delivery tube;
   screwing helical or spiral anchor into the heart tissue;
   adjusting the orientation of the ventricular function assisting device according to the internal anatomy of the ventricle;
   discharging the ventricular function assisting device by retracting delivery tube proximally such that arms of the ventricular function assisting device change into a deployed preloaded conformation as the arms of the ventricular assisting device become pressed against the internal walls of the ventricle;
   retracting distally the delivery tube;
   releasing the attachment between the torque tube and the anchoring element; and retracting proximally the delivery tube with the torque wire and guidewire inside the delivery tube.

* * * * *